US008911723B2

(12) United States Patent
Hantash et al.

(10) Patent No.: US 8,911,723 B2
(45) Date of Patent: Dec. 16, 2014

(54) HYBRID HYDROGEL SCAFFOLD COMPOSITIONS AND METHODS OF USE

(75) Inventors: Basil M. Hantash, East Palo Alto, CA (US); Ying Wang, Nanjing (CN)

(73) Assignee: Escape Therapeutics, Inc., San Jose, CA (US)

( * ) Notice: Subject to any disclaimer, the term of this patent is extended or adjusted under 35 U.S.C. 154(b) by 0 days.

(21) Appl. No.: 13/592,473

(22) Filed: Aug. 23, 2012

(65) Prior Publication Data

US 2013/0115196 A1 May 9, 2013

Related U.S. Application Data

(63) Continuation of application No. PCT/US2011/028638, filed on Mar. 16, 2011.

(60) Provisional application No. 61/314,265, filed on Mar. 16, 2010.

(51) Int. Cl.
*A61K 9/00* (2006.01)
*A61K 38/08* (2006.01)
*A61K 47/34* (2006.01)
*A61K 35/12* (2006.01)
*C12N 5/00* (2006.01)

(52) U.S. Cl.
CPC .............. *C12N 5/0068* (2013.01); *A61K 47/34* (2013.01); *A61K 38/08* (2013.01); *C12N 2533/50* (2013.01); *C12N 2533/30* (2013.01); *C12N 2533/78* (2013.01)
USPC ........................................ 424/93.7; 435/377

(58) Field of Classification Search
None
See application file for complete search history.

(56) References Cited

U.S. PATENT DOCUMENTS

| 2002/0160471 A1 | 10/2002 | Kisiday et al. |
| 2006/0198865 A1* | 9/2006 | Freyman et al. ............. 424/423 |
| 2008/0182287 A1 | 7/2008 | Smith et al. |
| 2008/0241250 A1 | 10/2008 | Emans et al. |
| 2009/0099091 A1 | 4/2009 | Hantash |

FOREIGN PATENT DOCUMENTS

WO  WO 2006036826 A2 *  4/2006

OTHER PUBLICATIONS

'Pluronic F127' accessed from http://worldaccount.basf.com/wa/NAFTA/Catalog/ChemicalsNAFTA/info/BASF/PRD/30085239 on Aug. 5, 2013.*
Kazunori Hamada, Motohiro Hirose, Toshihiko Yamashita, Hajime Ohgushi, Spatial distribution of mineralized bone matrix produced by marrow mesenchymal stem cells in self-assembling peptide hydrogel scaffold, 2008, Journal of Biomedical Materials Research Part A, vol. 84A, Issue 1, pp. 128-136.*

(Continued)

*Primary Examiner* — Blaine Lankford
*Assistant Examiner* — Trent R Clarke
(74) *Attorney, Agent, or Firm* — Wilmer Cutler Pickering Hale and Dorr LLP

(57) ABSTRACT

The present invention includes new hybrid hydrogel scaffolds comprised of a polyoxyethylene-polyoxypropylene (block) copolymer (a "poloxamer") and a self-assembling peptide, which maintain the mechanical and bioactive properties of its individual constituents (as compared to when the individual constituents are scaffolds or hydrogels by themselves). The hydrogels of the invention can include a combination of materials from different origins or with different properties that provides a hybrid material that meets the multiple needs of a scaffold for tissue engineering.

4 Claims, 11 Drawing Sheets

(56) References Cited

OTHER PUBLICATIONS

K.H. Chua, B.S. Aminuddin, N.H. Fuzina and B.H.I. Ruszymah, Insulin-Transferrin-Selenium Prevent Human Chondrocyte Dedifferentiation and Promote the Formation of High Quality Tissue Engineered Human Hyaline Cartilage, 2005, European Cells and Materials vol. 9, pp. 58-67.*

Ruszymah Binti Haji Idrus, Kienhui Chua, Mazlyzam Abdul Latif, Fuzina Nor Hussein, Aminuddin Bin Saim, Formation of in vivo tissue engineered human hyaline cartilage in the shape of a trachea with internal support, 2005, International Journal of Pediatric Otorhinolaryngology, vol. 69, pp. 1489-1495.*

Abu Ubeid A, Zhao L, Wang Y, Hantash BM. Short-Sequence Oligopeptides with Inhibitory Activity against Mushroom and Human Tyrosinase. J Invest Dermatol 2009; 129:2242-9, 8 pages.

Caplan MR et al., "Effects of systematic variation of amino acid sequence on the mechanical properties of a self-assembling, oligopeptide biomaterial," *J Biomater Sci Polym Ed*, 2002, 13(3):225-236, 12 pages.

Cortiella J et al., "Tissue-engineered lung: an in vivo and in vitro comparison of polyglycolic acid and pluronic F-127 hydrogel/somatic lung progenitor cell constructs to support tissue growth," *Tissue Eng*, May 2006, 12(5):1213-1225, 13 pages.

DiBiase MD, Rhodes CT, "Investigations of epidermal growth factor in semisolid formulations," *Pharm Acta Helv* 1991, 66(5-6):165-169, 7 pages.

Dominici M et al. Minimal Criteria for Defining Multipotent Mesenchymal Stromal Cells. The International Society for Cellular Therapy Position Statement:, Cytotherapy, 8(4):315-317, 2006, 3 pages.

Escobar-Chavez JJ, et al., "Applications of thermo-reversible pluronic F-127 gels in pharmaceutical formulations," *J Pharm Pharm Sci* 2006, 9(3): 339-358, 20 pages.

Hata K et al., "A CCAAT/enhancer binding protein beta isoform, liver-enriched inhibitory protein, regulates commitment of osteoblasts and adipocytes," *Mol Cell Biol*, 2005, 25(5):1971-1979, 10 pages.

Hemmrich, K et al., "Implantation of preadipocyte-loaded hyaluronic acid-based scaffolds into nude mice to evaluate potential for soft tissue engineering," *Biomaterials*, 2005, 26(34):7025-37, 13 pages.

Holmes TC et al., "Extensive neurite outgrowth and active synapse formation on self-assembling peptide scaffolds," *Proc Natl Acad Sci USA*, 2000, 97(12):6728-6733, 6 pages.

International Search Report and Written Opinion for International Patent Application No. PCT/US11/28638 mailed Aug. 25, 2011. 15 pages.

Kisiday J et al., "Self-assembling peptide hydrogel fosters chondrocyte extracellular matrix production and cell division: implications for cartilage tissue repair," *Proc Natl Acad Sci USA*, 2002, 99(15):9996-10001, 7 pages.

Leon EJ et al., "Mechanical properties of a self-assembling oligopeptide matrix," *J Biomater Sci Polym Ed*, 1998, 9(3):297-312, 16 pages.

Liu Y et al., "Repairing large porcine full-thickness defects of articular cartilage using autologous chondrocyte-engineered cartilage," *Tissue Eng*, 2002, 8(4):709-721, 13 pages.

Miyazaki S, et al., "Pluronic F-127 gels as a vehicle for topical administration of anticancer agents," *Chem Pharm Bull* (Tokyo) 1984, 32(10):4205-4208, 4 pages.

Niu et al., "Synthesis and Characterization of Reactive Poloxamer 407s for Biomedical Applications", *J. Controlled Release*, 2009, 137:49-56, 8 pages.

Semino CE et al., "Entrapment of migrating hippocampal neural cells in three-dimensional peptide nanofiber scaffold," *Tissue Eng*, 2004, 10(3-4):643-655, 13 pages.

Semino CE et al., "Functional differentiation of hepatocyte-like spheroid structures from putative liver progenitor cells in three-dimensional peptide scaffolds," *Differentiation*, 2003, 71:262-270, 9 pages.

Vashi AV et al., "Adipose differentiation of bone marrow-derived mesenchymal stem cells using Pluronic F-127 hydrogel in vitro," *Biomaterials*, 2008, 29(5):573-579, 7 pages.

Zhang et al., "Design of nanostructured biological materials through self-assembly of peptides and proteins," *Curr Opin Chem Biol* 2002;6:865-71, 7 pages.

Zhang S et al., "Self-complementary oligopeptide matrices support mammalian cell attachment. Biomaterials," 1995, 16(18):1385-1393, 9 pages.

Zhang S et al., "Spontaneous assembly of a self-complementary oligopeptide to form a stable macroscopic membrane," *Proc Natl Acad Sci USA*, 1993, 90(8): 3334-3338, 6 pages.

Zhang S, "Fabrication of novel biomaterials through molecular self-assembly," *Nat Biotechnol*, 2003, 21(10):1171-1178, 8 pages.

Zhao L et al., "TGF-beta1 Induces Osteogenic Differentiation of Murine Bone Marrow Stromal Cells," *Tissue Eng Part A, 16*(2):725-733, 2009, 9 pages.

Butala, et al., "Endogenous Stem Cell Therapy Enhances Fat Graft Survival", Plastic and Reconstructive Surgery Journal, 130(2):293-306, Aug. 2012, 14 pages.

Chan, et al., "Scaffolding in Tissue Engineering: General Approaches and Tissue-Specific Considerations", Eur. Spine J., 17(Suppl 4):S467-S479, published online Nov. 13, 2008, 13 pages.

Grieshaber, et al., "Assembly Properties of an Alanine-Rich Lysine-Containing Peptide and the Formation of Peptide/Polymer Hybrid Hydrogels", Macromolecular Chemistry and Physics, 212:229-239, Feb. 1, 2011, 11 pages.

Gunatillake, et al., "Biodegradable Synthetic Polymers for Tissue Engineering", European Cells and Materials, 5:1-16, May 2003, 16 pages.

Huang, et al., "In vivo Differentiation of Adipose-Derived Stem Cells in an Injectable Poloxamer-Octapeptide Hybrid Hydrogel", Tissue and Cell, 43:344-349, available online Sep. 6, 2011, 6 pages.

Wang, et al., "Support of Human Adipose-Derived Mesenchymal Stem Cell Multipotency by a Poloxamer-Octapeptide Hybrid Hydrogel", Biomaterials, 31:5122-5130, available online Mar. 26, 2010, 9 pages.

* cited by examiner

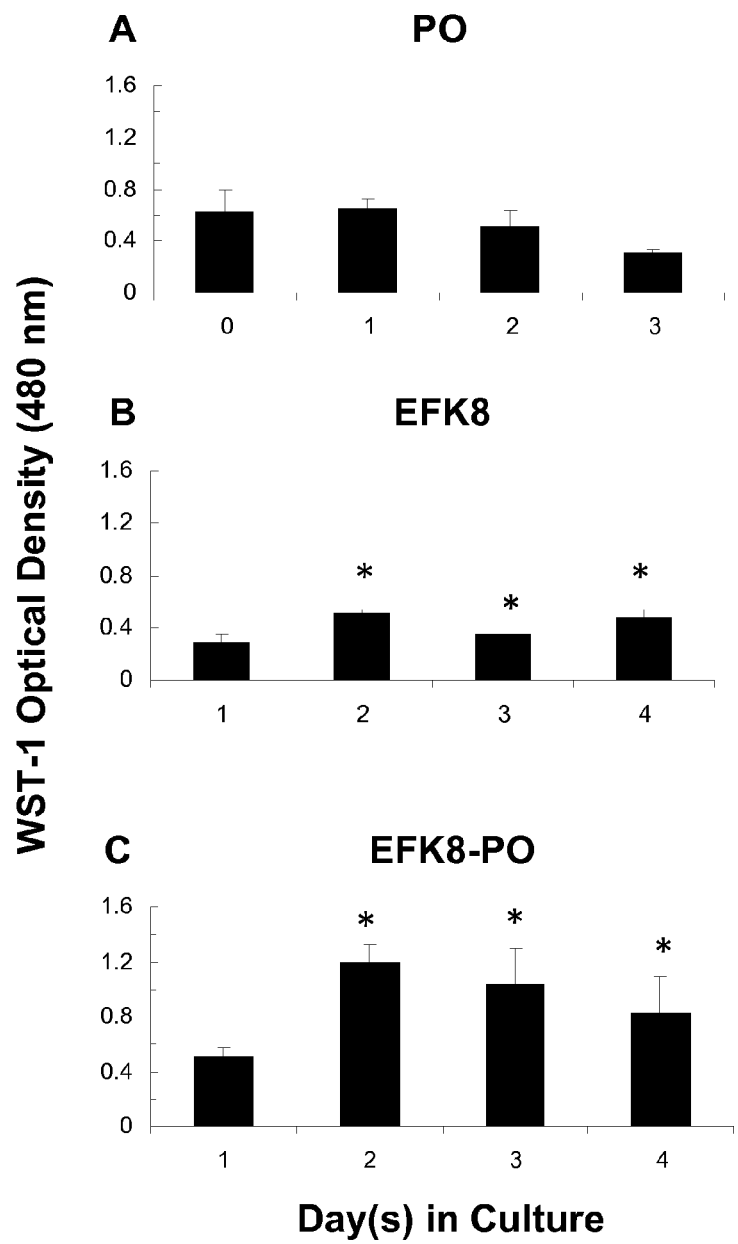
FIG. 4A-C

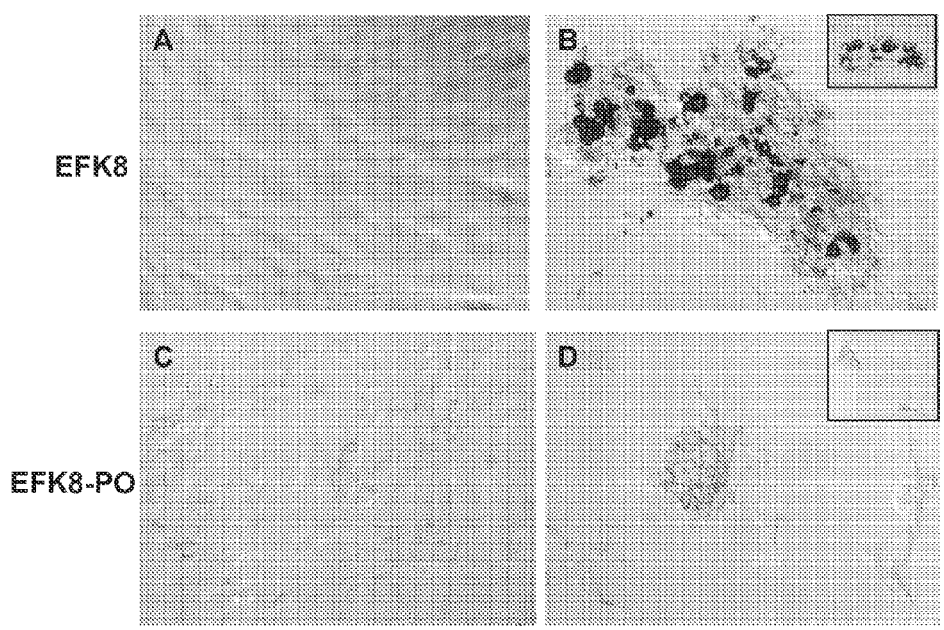
FIG. 5A-D

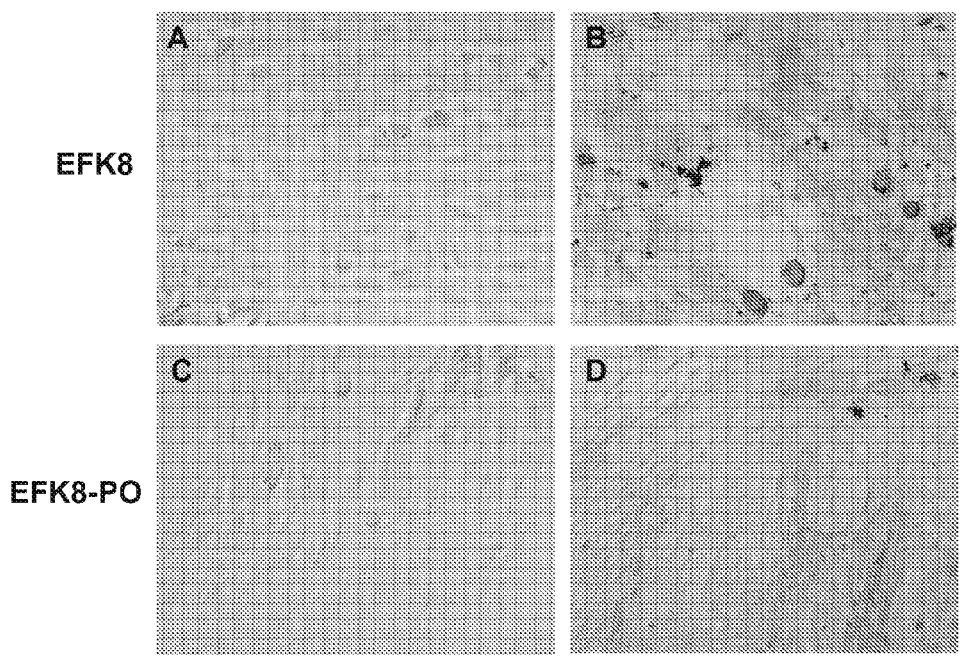
FIG. 6A-D

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Phe Glu Phe Lys Phe Glu Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Phe Glu Phe Lys Phe Glu Phe Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ala Asp Ala Arg Ala Asp Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Arg Ala Asp Ala Asp Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Glu Ala Lys Ala Glu Ala Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Glu Ala Arg Ala Glu Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Asp Ala Lys Ala Asp Ala
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Glu Ala Glu Ala His Ala His
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Glu Leu Glu Leu Lys Leu Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Glu Ala Glu Ala Lys Ala Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Glu His Glu His Lys His Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Lys Phe Glu Phe Lys Phe Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Glu Phe Lys Phe Glu Phe Lys Phe
1               5
```

HYBRID HYDROGEL SCAFFOLD COMPOSITIONS AND METHODS OF USE

CROSS-REFERENCE TO RELATED APPLICATIONS

This application is a continuation of International Application PCT/US11/28638, filed Mar. 16, 2011, which claims priority to U.S. Provisional Application No. 61/314,265, filed Mar. 16, 2010, both of which are incorporated herein by reference.

BACKGROUND OF THE INVENTION

The development of new biological materials, particularly those capable of serving as permissive substrates for cell growth, differentiation, and biological function, is a key area for advancing medical technology. Recently, attempts have been made to develop new biologically compatible scaffolds for controlled drug release, tissue repair, and tissue engineering. Since many diseases cannot be treated solely by small molecule drugs, researchers have begun investigating the potential role of biomaterials alone or in combination with cell-based therapies as an alternative therapeutic strategy.

Poloxamer 407 (pluronic F-127, PF-127) is a thermoreversible scaffold composed of polyoxyethylene-polyoxypropylene copolymers in a concentration ranging from 20-30%. (Miyazaki S, et al., "Pluronic F-127 gels as a vehicle for topical administration of anticancer agents," *Chem Pharm Bull* (Tokyo) 1984, 32(10):4205-4208.) The amphiphilic nature of poloxamer 407 can allow its use as a drug carrier in a variety of settings including administration by oral, topical, intranasal, vaginal, rectal, ocular, and parenteral routes. (Escobar-Chavez J J, et al., "Applications of thermo-reversible pluronic F-127 gels in pharmaceutical formulations," *J Pharm Pharm Sci* 2006, 9(3): 339-358.) The potential use of poloxamer 407 as an artificial skin has been reported, and there have been several studies on use of poloxamer 407 for in vivo tissue engineering of cartilage and lung. (DiBiase Md., Rhodes Conn., "Investigations of epidermal growth factor in semisolid formulations," *Pharm Acta Helv* 1991, 66(5-6): 165-169; Liu Y et al., "Repairing large porcine full-thickness defects of articular cartilage using autologous chondrocyte-engineered cartilage," *Tissue Eng,* 2002, 8(4):709-721; Cortiella J et al., "Tissue-engineered lung: an in vivo and in vitro comparison of polyglycolic acid and pluronic F-127 hydrogel/somatic lung progenitor cell constructs to support tissue growth," *Tissue Eng,* 2006 May, 12(5):1213-1225.)

It appears that poloxamer 407 not only facilitates tissue formation but also can be important for proper tissue assembly. (Cortiella et al. (2006).) Poloxamer 407 has also been reported to provide a 3D environment for differentiation of bone marrow-derived mesenchymal stem cells (BMSCs) into adipocytes, providing a potential alternative cell source for adipose tissue engineering. (Vashi A V et al., "Adipose differentiation of bone marrow-derived mesenchymal stem cells using Pluronic F-127 hydrogel in vitro," *Biomaterials,* 2008, 29(5):573-579). The thermoreversible and promising drug release characteristics of poloxamer 407 render it an attractive candidate as a hydrogel scaffold for tissue engineering. However, because it is a completely synthetic and nonionic polymer, cells embedded in poloxamer 407 become unevenly distributed and clustered after several days of culture even when combined with collagen. (Id.) This characteristic can severely limit its potential use as a biomaterial in medical applications.

A class of biomaterials comprised of spontaneously self-assembling short (8-24 amino acids) ionic complementary oligopeptides has been described. (Zhang S, "Fabrication of novel biomaterials through molecular self-assembly," *Nat Biotechnol,* 2003, 21(10):1171-1178; which is hereby incorporated by reference in its entirety, including all description on the peptides.) Self-assembling peptides form stable β-sheet structures when dissolved in deionized water. Exposure to electrolyte solutions initiates β-sheet assembly into interweaving nanofibers, producing a hydrogel containing up to >99% water content. (Zhang S et al., "Spontaneous assembly of a self-complementary oligopeptide to form a stable macroscopic membrane," *Proc Natl Acad Sci USA,* 1993, 90(8): 3334-3338; Zhang S et al., "Self-complementary oligopeptide matrices support mammalian cell attachment. Biomaterials," 1995, 16(18):1385-1393; Holmes T C et al., "Extensive neurite outgrowth and active synapse formation on self-assembling peptide scaffolds," *Proc Natl Acad Sci USA,* 2000, 97(12):6728-6733; which are hereby incorporated by reference in their entirety, including any disclosure on peptides and methods for forming hydrogels). The structure of such nanofibers is about 3 orders of magnitude smaller than most polymer microfibers. (Kisiday J et al., "Self-assembling peptide hydrogel fosters chondrocyte extracellular matrix production and cell division: implications for cartilage tissue repair," *Proc Natl Acad Sci USA,* 2002, 99(15):9996-10001.) This important feature helps support cell attachment and differentiation of a variety of mammalian primary and transformed cells, such as neurons, chondrocytes, and microvascular endothelial cells. (Zhang et al., (1995); Kisiday et al., (2002); Semino C E et al., "Functional differentiation of hepatocyte-like spheroid structures from putative liver progenitor cells in three-dimensional peptide scaffolds," *Differentiation,* 2003, 71(4-5):262-270; Semino C E et al., "Entrapment of migrating hippocampal neural cells in three-dimensional peptide nanofiber scaffold," *Tissue Eng,* 2004, 10(3-4):643-655.)

This class of biomaterial has several advantages when used as a scaffold for tissue engineering. First, such a nanofiber network resembles ECM and provides a truly 3-D environment for cells to grow, migrate, proliferate and differentiate. Second, biomolecules in such a nanoscale environment diffuse slowly and are likely to establish a local molecular gradient more closely mimicking the in vivo scenario. Third, the degradation products of such peptide scaffolds are naturally occurring amino acids, potentially reducing their cytotoxicity. (Holmes et al. (2000).) In addition, the mechanical strength as well as chemical composition of the scaffold can be controlled through manipulation of peptide parameters. (Holmes et al. (2000); Leon E J et al., "Mechanical properties of a self-assembling oligopeptide matrix," *J Biomater Sci Polym Ed,* 1998, 9(3):297-312; Caplan M R et al., "Effects of systematic variation of amino acid sequence on the mechanical properties of a self-assembling, oligopeptide biomaterial," *J Biomater Sci Polym Ed,* 2002, 13(3):225-236; which are hereby incorporated by reference including disclosure relating to the relationship between peptide composition and length with mechanical strength or definition of structure.)

In terms of amino acid length, shorter peptides offer the advantage of lower cost, greater ease of synthesis, and higher solubility and purity. Furthermore, shorter peptides show less structural and chemical complexity, which facilitates their study. On the other hand, shorter peptides are less stable than longer ones, do not form well-ordered structures, and show fewer tendencies for self-assembly. They demonstrate variable solubility in water and sometimes precipitate into disordered aggregates. Researchers have concluded that designing shorter self-assembling peptides with well-defined structures represents a serious challenge (Leon et al., 1998).

EFK8 is one of the smallest peptides in this new family of biomaterials originally discovered by Zhang et al. (1993). EFK8 has an amino acid sequence that alternates between hydrophobic side chains and charged side chains, forming a special left-hand double helix that spontaneously undergoes association under physiological conditions (Zhang et al., "Design of nanostructured biological materials through self-assembly of peptides and proteins," Curr Opin Chem Biol 2002; 6:865-71.).

SUMMARY OF THE INVENTION

In tissue engineering, the scaffold should provide a microenvironment that supports cell attachment, proliferation and differentiation, migration, tissue regeneration and appropriate 3-D organization. However, scaffolds made of a single component or a single phase usually cannot provide such an ideal microenvironment that meets all or most of the above requirements. The combination of materials from different origins or with different properties could generate a hybrid material that meets the multiple needs of a scaffold for tissue engineering. The development of new biological materials, particularly those capable of serving as permissive substrates for cell growth, differentiation, and biological function, is a key area for advancing medical technology.

In its main embodiments, the present invention provides new hybrid hydrogel scaffolds comprised of a polyoxyethylene-polyoxypropylene (block) copolymer (referred to herein as a "poloxamer") and a self-assembling peptide, which maintain the mechanical and bioactive properties of its individual constituents (as compared to when the individual constituents are scaffolds or hydrogels by themselves). As used herein, a "hybrid hydrogel" includes at least one poloxamer and at least one self-assembling peptide. However, the hydrogels of the invention are not limited to hybrid hydrogels. Rather, a "hydrogel" of the invention not only includes hybrid hydrogels, but also hydrogels that do not include a self-assembling peptide and are made from one or more poloxamers and one or more elements that contribute in some form to the structure and/or function of the hydrogel. Further, although the present hydrogels may sometimes be referred to as "hydrogel scaffolds," this is not meant to limit the application of the hydrogels for use as scaffolds in tissue engineering. Rather, a scaffold simply refers to the non-limiting use of the hydrogel as a three-dimensional structure, whether for tissue engineering, drug delivery, and the like. In fact, in some aspects, the hydrogels of the invention can be used as two-dimensional coatings for cell growth, maintenance and/or differentiation in tissue-culture applications.

Poloxamers include, but are not limited to, thermoreversible nonionic triblock copolymers composed of a central hydrophobic chain of polyoxypropylene (poly(propylene oxide)) ("PPO") flanked by two hydrophilic chains of polyoxyethylene ("PEO"), i.e., PEO-PPO-PEO. Specific poloxamers that can be used include, but are not limited to, Poloxamer 124 (Pluronic L44 NF), Poloxamer 188 (Pluronic F68 NF), Poloxamer 237 (Pluronic F 87 NF), Poloxamer 338 (Pluronic F108 NF), and Poloxamer 407 (Pluronic F127 NF). In other aspects, the hybrid hydrogel scaffolds can comprise a combination of one or more different poloxamers.

In one aspect, the hydrogel comprises a poloxamer that is thermoreversible. For example, in one aspect, the poloxamer in solution is in liquid form at temperatures lower than room temperature, but is in gel form at room temperature or at body temperature. Where the poloxamer is thermoreversible, the poloxamer and additional components are mixed in an aqueous solution at a temperature that prevents a phase transition from liquid to gel. The mixed solution is then allowed to transition to gel state at higher temperatures. As used herein, the hydrogels of the invention generally include an aqueous component even if not explicitly specified herein. The aqueous component can comprise, for example, water, phosphate buffered saline (PBS), and/or a solvent.

In certain aspects, with respect to the structural elements of the scaffold (i.e., not with respect to non-structural elements, such as salts, water, cells, small molecules, or large biologic molecules), any hybrid hydrogel of the invention can consist only of one or more different types of poloxamer and one or more different types of self-assembling peptide.

In other aspects, the hybrid hydrogel scaffolds of the invention can further comprise one or more of the following: agarose, alginate, methylcellulose, carboxymethylcellulose, hydroxypropylmethylcellulose, and bioactive molecules.

As used herein, bioactive molecules include, but not limited to, small molecules, proteins, peptides, sugars, and nucleic acids. Proteins can include for example growth factors, anti-differentiation factors, differentiation factors, cytokines, antibodies, hormones, extracellular matrix proteins (such as collagen, vitronectin, fibrin, etc.), extracellular matrix sugars, morphogenic signals, chemoattractants, etc. One example of an anti-differentiation factor is Y-27632, the selective Rho-associated kinase inhibitor 1. Nucleic acids can include siRNA, shRNA, antisense molecules, plasmids, etc. The hydrogels of the invention can also comprise viruses for gene expression or attenuated viruses in the context of vaccines. The hydrogels of the invention can also comprise nutrients, minerals, and other deliverables.

In some aspects, the hydrogels of the invention are made from at least a poloxamer(s) and one or more of: a self-assembling peptide(s), agarose, alginate, methylcellulose, carboxymethylcellulose, hydroxypropylmethylcellulose, and/or bioactive molecules.

In one aspect, a hydrogel of the invention can comprise a poloxamer that has an approximate average molecular weight between about 9,000 and 15,000 g/mol. In one aspect, the hydrogel comprises a poloxamer that has an average molecular weight between about 10,000 and 14,000 g/mol, or between about 11,000 and 13,000 g/mol, or between about 11,500 and 13,000 g/mol, or between about 12,000 and 13,000 g/mol. In one aspect, the hydrogel comprises a poloxamer that has an average molecular weight that is about 12,500 g/mol. With respect to average molecular weight, the term "about" means ±1,000 g/mol.

In one aspect, the poloxamer has a polyoxyethylene content between about 60-85% by weight in volume ("w/v"). In another aspect, the poloxamer has a polyoxyethylene content between about 65-75%. In one aspect, the poloxamer has a polyoxyethylene content of about 70%. With respect to PPO or PEO content, the term "about" means ±1%.

In other aspects, the hybrid hydrogel scaffolds comprise a poloxamer having the following general chemical structure hereafter referred to as Formula I:

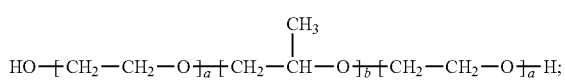

wherein "a" represents the ethylene oxide portion and "b" represents the propylene oxide portion. In one aspect, the ratio of "a" to "b" is about 2:1. In another aspect, the ratio of "a" to "b" is about 3:1. In another aspect, the total number of "a" in the above formula is 101 and the total number of "b" in the above formula is 56. In another aspect, the total number of "a" in the above formula is about 141 and the total number of "b" in the above formula is about 44.

In another aspect, the hydrogels of the invention comprise a poloxamer having a PEO-PPO-PEO triblock structure. In another aspect, the hydrogel can comprise a poloxamer having a PPO-PEO-PPO triblock structure.

In one aspect, the invention provides a hydrogel comprising a poloxamer and a self-assembling peptide, wherein the self-assembling peptide is between about 8 and about 24 amino acids in length. In one aspect, the self-assembling peptide is between about 8 and about 12 amino acids in length. In one aspect, the self-assembling peptide is between 8-10 amino acids in length. In one aspect, the self-assembling peptide is 8 amino acids in length.

In another aspect, the invention provides hydrogels comprising one or more modified poloxamers. For example, a modified poloxamer can include acrylate modified poloxamer 407 and thiol modified poloxamer 407. (See Niu et al., *J. Controlled Release*, 2009, 137:49-56, which is hereby incorporated by reference for at least its disclosure on modified poloxamers.) Niu (2009) reports that acrylate and thiol modified poloxamer 407 allowed for a liquid to gel transition at body temperature with a hydrogel having a concentration of poloxamer 407 as low as 17.5% by weight. The reaction between acrylate and thiol modified poloxamers created a crosslinking structure that purportedly increased stability of the hydrogel.

In one aspect, the invention provides a hybrid hydrogel scaffold comprising of a polyoxyethylene-polyoxypropylene copolymer and a self-assembling peptide, wherein the self-assembling peptide is 8 amino acids in length and is present in an amount of less than about 1% by weight in volume (w/v) of solution.

In one aspect, the hybrid hydrogel scaffold comprises poloxamer 407 ("PO") and self-assembling oligopeptide EFK8, and when the scaffold comprises PO and EFK8, the scaffold is referred to herein as "EFK8-PO" or "MorphoGel™".

In one aspect, the invention provides a hybrid hydrogel scaffold comprising PO and EFK8, wherein the percentage of EFK8 (weight % in solution) is less than about 5%, 4%, 3%, 2%, 1%, or less than about 1%; wherein "about" as used in this aspect means a variation of less than 0.1 percent), and wherein the scaffold is capable of supporting hAMSC proliferation and/or differentiation or is capable of supporting proliferation of cell-types that require extracellular matrix contact in their native environment.

In one aspect, the invention provides a hybrid hydrogel scaffold comprising PO and EFK8, wherein the percentage of PO (weight % in solution) is about 30%, 25%, 24%, 23%, 22%, 21%, 20%, 19%, 18%, 17%, 16%, 15%, or less than 15%; wherein "about" as used in this aspect means a variation of less than 1 percent). In one aspect, the scaffold is capable of supporting hAMSC proliferation and/or differentiation or is capable of supporting proliferation of cell-types that require extracellular matrix contact in their native environment. In one aspect, the scaffold is the state of a gel at body temperature.

In one aspect, the invention provides a hydrogel scaffold comprising: (a) less than about 15% (w/v) of a poloxamer having an average molecular weight between about 11,000 and 14,000 g/mol and (b) methylcellulose.

In one aspect, the invention provides a hybrid hydrogel scaffold comprising PO and EFK8, wherein the content of PO is about 20% PO (w/v) and the content of EFK8 is about 1% (w/v), and wherein the scaffold is capable of supporting hAMSC differentiation.

In one aspect, the invention provides a hybrid hydrogel scaffold consisting essentially of PO and EFK8. As used herein, the term "consisting essentially of" refers to the presence of self-assembling peptides and/or poloxamers in the hybrid hydrogel scaffold, and not to the presence of small molecules or macromolecules or other molecules that may be delivered in the scaffold and are intended to have a cellular, molecular, and/or therapeutic effect, and not to the presence of excipients or inert ingredients or the liquid component.

In one aspect, the invention provides a hybrid hydrogel scaffold comprising PO and EFK8, wherein the ratio of PO to EFK8 is between about 100:1 and 5:1 (where the ratio is with respect to the % w/v of PO and the % w/v of EFK8). In one aspect, the invention provides a hybrid hydrogel scaffold comprising PO and PE, wherein the ratio of PO to EFK8 is at least about 50:1, 40:1, 30:1, 25:1, 24:1, 23:1, 22:1, 21:1, 20:1, 19:1, 18:1, 17:1, 16:1, 15:1, 10:1, 5:1, 4:1, 3:1, and 2:1. These scaffolds support cellular proliferation at a rate as great as one supported by a scaffold consisting of EFK8 alone. Further, these scaffolds can support differentiation substantially similar to a scaffold consisting of EFK8 alone when exposed to the appropriate induction medium.

In one aspect, the hybrid hydrogel scaffold comprises the characteristic of having a storage modulus G' that is at least about 4 orders of magnitude greater than the storage modulus G' of a hydrogel made of the self-assembling peptide component alone at 37° C.

In one aspect, the storage modulus of a hybrid hydrogel scaffold comprising PO and EFK8 is greater by at least about 4 orders of magnitude as compared to a hydrogel made with EFK8 alone (no PO). The storage modulus can be determined by rheological tests as described herein.

In one aspect, the hybrid hydrogel scaffold comprises the characteristic of having a lost storage modulus G''' that is at least about 3 orders of magnitude greater than the lost storage modulus G'' of a hydrogel made of the copolymer component alone at 37° C.

In one aspect, where the hybrid hydrogel scaffold comprises encapsulated cells, the scaffold comprises the characteristic of having a greater homogeneous dispersion of the cells as compared to a hydrogel made from the copolymer component alone.

In one aspect, the invention provides a hybrid hydrogel scaffold comprising: (1) polyoxypropylene blocks at a micelle center, (2) hydrophilic polyoxyethylene blocks surrounded by water, and (3) a self-assembled peptide nanofibrillar network.

In one aspect, the invention provides a hybrid hydrogel scaffold comprising a self-assembling peptide with an amino acid sequence that alternates between hydrophobic side chains and charged side chains. In one aspect, this self-assembling peptide is an eight-amino acid length oligopeptide. In one aspect, this self-assembling peptide forms a left-hand double helix.

In one aspect, the hybrid hydrogel scaffold of the invention is made from the co-gelation of the copolymer with the self-assembling oligopeptide.

In one aspect, the hybrid hydrogel scaffolds of the invention can be used as a matrix/scaffold for tissue engineering applications (bone, as a skin substitute, etc).

In one aspect, the hybrid hydrogel scaffolds of the invention can be used as a two-dimensional cell growth matrix, whereby the appropriate tissue culture dish/flask/well/plate/etc. is coated with a layer of the hybrid hydrogel for growth of cells, including but not limited to ES cells, iPS cells, MSCs, HSCs, or other stem or somatic cells. An advantage of using a thermoreversible poloxamer for 2-D tissue culture is that the poloxamer can prevent the use of trypsin or dispase or collegenase, etc. For example, the hybrid hydrogel can be coated onto the tissue culture platform, and when the cells that are growing on the coated platform are ready for passaging, the platform can be placed at a low temperature (such as 4° C.) sufficient to cause the hydrogel to transition from gel to liquid form. The cells and media can be collected and centrifuged (at the low temperature) to separate the cells from the media and the hydrogel in liquid form.

In one aspect, the hybrid hydrogel scaffolds of the invention can be used to reduce scar formation post-injury or trauma.

In one aspect, the hybrid hydrogel scaffolds of the invention can be used to improve the appearance of preexisting scars.

In one aspect, the hybrid hydrogel scaffolds of the invention can be used as a tissue filler agent for volume restoration of tissue defects.

In one aspect, the hybrid hydrogel scaffolds of the invention can be used to reverse the signs of skin aging or reduce volume loss of skin.

In one aspect, the hybrid hydrogel scaffolds of the invention can be combined with growth factors or small molecules, nutrients, minerals, etc, to recapitulate the environment in vivo for a scaffold. In such an aspect, these materials can be encapsulated into the scaffold using the same methods for encapsulating cells in vitro as described herein.

In one aspect, the hybrid hydrogel scaffolds of the invention can be used as a delivery mechanism for drugs, proteins, peptides, small molecules, nutrients, minerals, polynucleotides, etc. The composition of the scaffolds of the invention can be varied to promote a specific controlled release.

In one aspect, the hybrid hydrogel scaffolds of the invention can be used as a delivery mechanism for somatic and stem cells in transplantation settings, disease, or injury.

In one aspect, the hybrid hydrogel scaffolds of the invention can be used as a hemostatic agent.

In one aspect, the invention provides a hydrogel consisting essentially of a self-assembling peptide (i.e., the scaffold does not include a copolymer) for use as a hemostatic agent. In one aspect, a hydrogel consisting of an EFK8 oligopeptide alone can also be used as a hemostatic agent.

In one aspect, the invention provides a hydrogel consisting essentially of poloxamer 407 for use in tissue engineering applications directed to compacted tissue, such as cartilage, lens, and osseous tissue. In another aspect, the invention provides a hybrid hydrogel comprising a ratio of poloxamer to self-assembling peptide sufficient to support aggregation of cells (from the poloxamer component), yet also sufficient to promote cell viability and attachment.

TABLE 1

Figure 2:
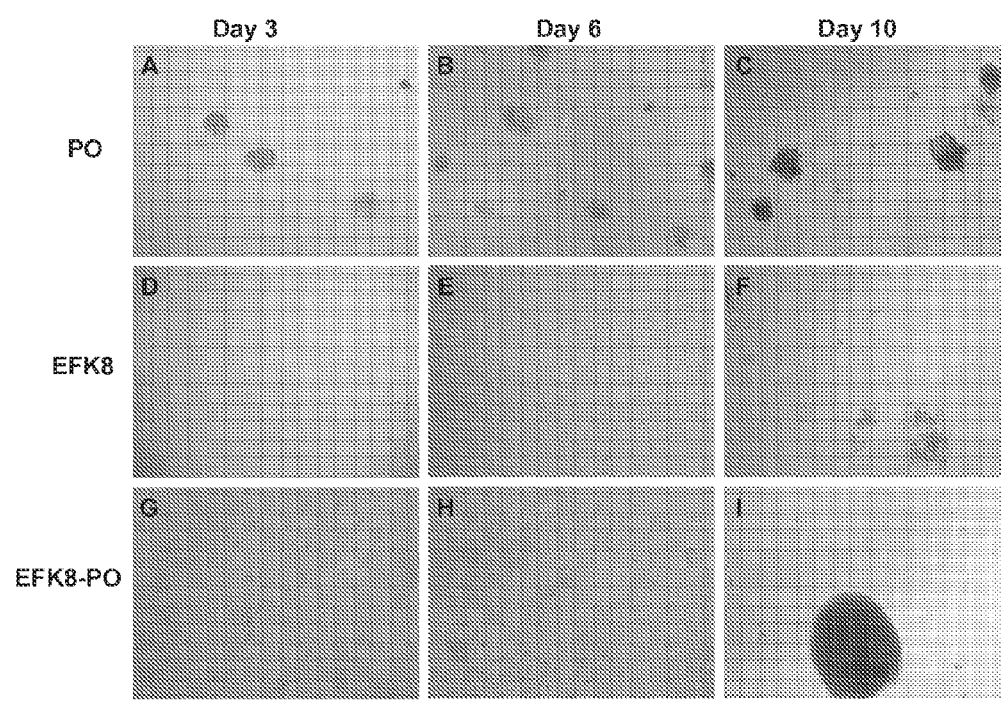
FIG. 2. hAMSC distribution after encapsulation in 3 different hydrogels. hAMSCs were encapsulated in PO (A-C), EFK8 (D-F), and EFK8-PO (G-I) hydrogels and cultured in the appropriate medium for 3, 6 or 10 days, respectively. See Table 1 below for a quantitative summary of FIG. 2 results. Original magnification×4.

Quantitative Summary of FIG. 2

| Hydrogel | Aggregation | | |
|---|---|---|---|
| | Day 3 | Day 6 | Day 10 |
| PO | >90% | >90% | >90% |
| EFK8 | <3-5% | <3-5% | ~10% |
| EFK8-PO | None | None | Rare |

Figure 3:
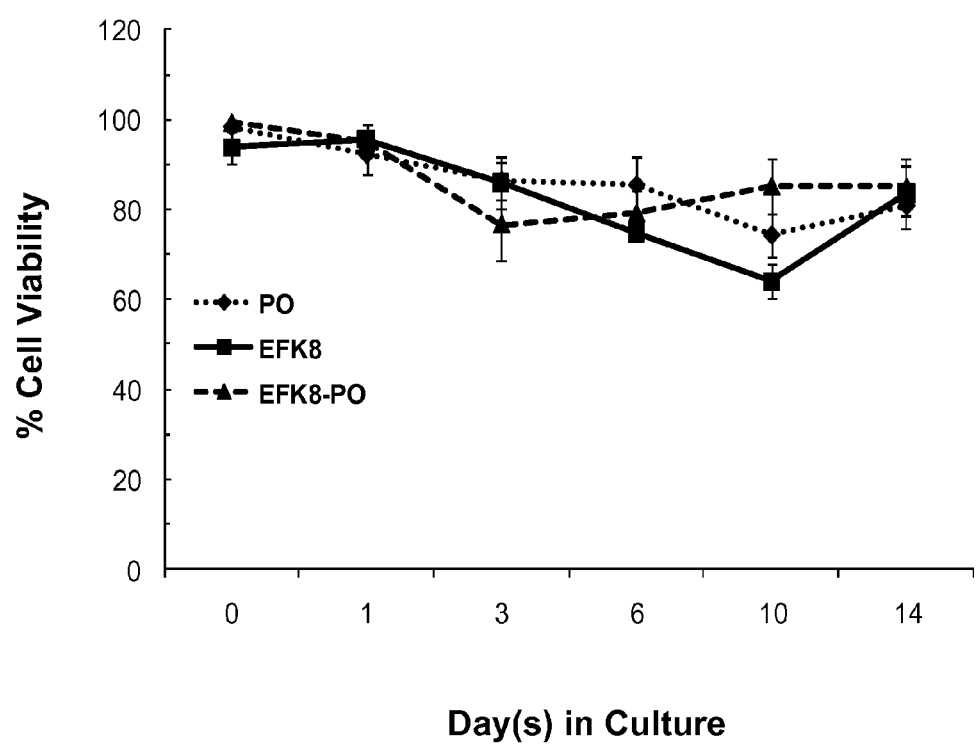

FIG. 3. Viability of hydrogel-encapsulated hAMSCs. hAMSCs maintained a viability of 80% or higher in all 3 hydrogels through 14 days of culture.

Figure 4D:
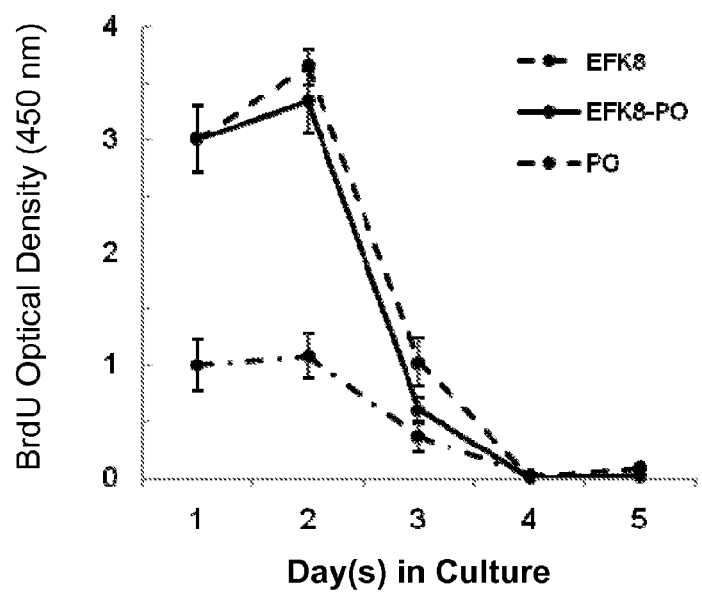

FIG. 4. Rate of proliferation of hydrogel-encapsulated hAMSCs. (A) No statistically significant difference was observed when cells were cultured in PO at each time point ($p>0.05$). However, proliferation of hAMSCs was found to be statistically significantly different when comparing days 2, 3, or 4 with day 1 in EFK8 (B) and EFK8-PO (C) hydrogels. (*$p<0.05$). FIG. 4D also compares the proliferation rates of hAMSCs cultured on PO, EFK8, and EFK8-PO hydrogels by a different assay (BrdU optical density at 450 nm).

FIG. 5. Adipogenic differentiation of hydrogel-encapsulated hAMSCs hydrogels in vitro. EFK8 (A) or EFK8-PO (B) encapsulated hAMSCs were cultured with DMEM alone for 7 days. EFK (C) or EFK8-PO (D) encapsulated hAMSCs were cultured with adipogenic differentiation medium for 7 days. Cells were then stained with Oil Red O, processed according to the materials and methods, and examined under light microscopy. Inset images in (B) and (D) illustrate positive staining (red color or dark black in black/white), indicating the presence of multiple lipid droplets. Original magnification×10. See also Table 2 below for a Quantitative Summary of FIGS. 5 and 6.

FIG. 6. Osteogenic differentiation of hydrogel-encapsulated hAMSCs hydrogels in vitro. EFK8 (A) or EFK8-PO (B) encapsulated hAMSCs were cultured with DMEM alone for 14 days. EFK8 (C) or EFK8-PO (D) encapsulated hAMSCs were cultured with osteogenic differentiation medium for 14 days. Cells were then stained for alkaline phosphatase (red color) [dark black in black & white photo], processed according to the materials and methods, and examined under light microscopy. Original magnification×10. See also Table 2 for a Quantitative Summary of FIGS. 5 and 6.

TABLE 2

Quantitative Summary of FIGS. 5 and 6

| | Adipogenic | | Osteogenic | |
|---|---|---|---|---|
| | Oil-Red-O (% +) | | AP (% +) | Alizarin Red (% +) |
| Hydrogel | Day 4 | Day 7 | Day 14 | |
| Control Media | 0% | 3% ± 5% | 6% ± 4% | 4% ± 3% |
| PO | n/a | n/a | n/a | n/a |
| EFK8 | 42 ± 6% | 68 ± 8% | 88 ± 9% | 54 ± 7% |
| EFK8-PO | 38 ± 3% | 56 ± 8% | 72 ± 6% | 46 ± 5% |

Figure 7:
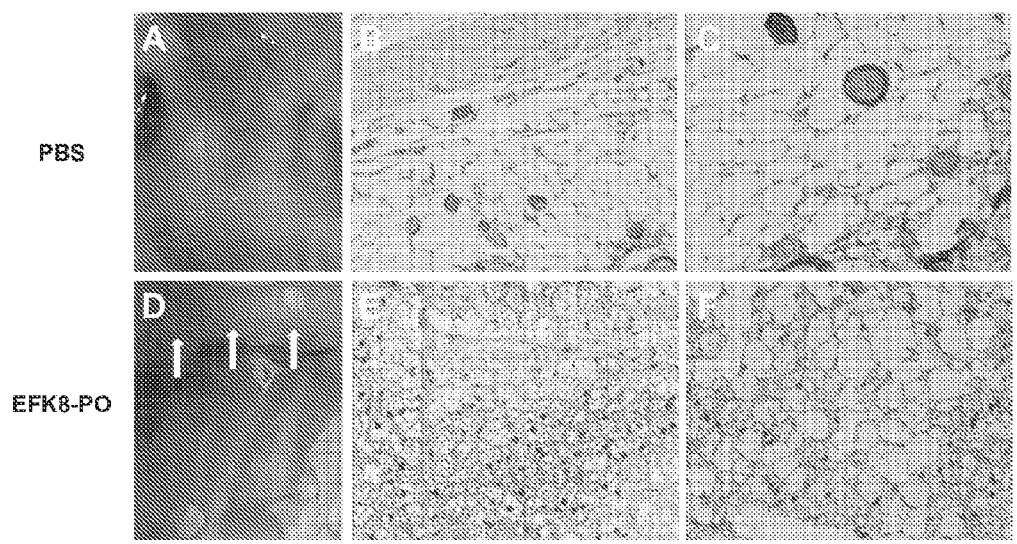

FIG. 7. Adipogenic differentiation of hydrogel-encapsulated hAMSCs in vivo. The fascial plane of the dorsal neck region of nude mice was exposed 30 days after treatment with either PBS (A) or EFK8-PO encapsulated hAMSCs (D). New fat tissue was observed in the EFK8-PO cohort (white arrows shown in D), but not in PBS (A) or the other hydrogels (data not shown). Fat tissue was then processed for immunohistochemical staining with a monoclonal antibody specific to human nuclei and slides were developed for diaminobenzidine staining (brown color). All slides were counterstained with hematoxylin (blue color). Human nuclei were observed in the EFK8-PO cohort (E & F) but not in PBS (B & C) or the other hydrogels (not shown). Original magnification×4 (A & D), 10 (B & E), or 20 (C & F). In black and white, diaminobenzidine and hematoxylin staining appear as darker grey/black.

Figure 8:
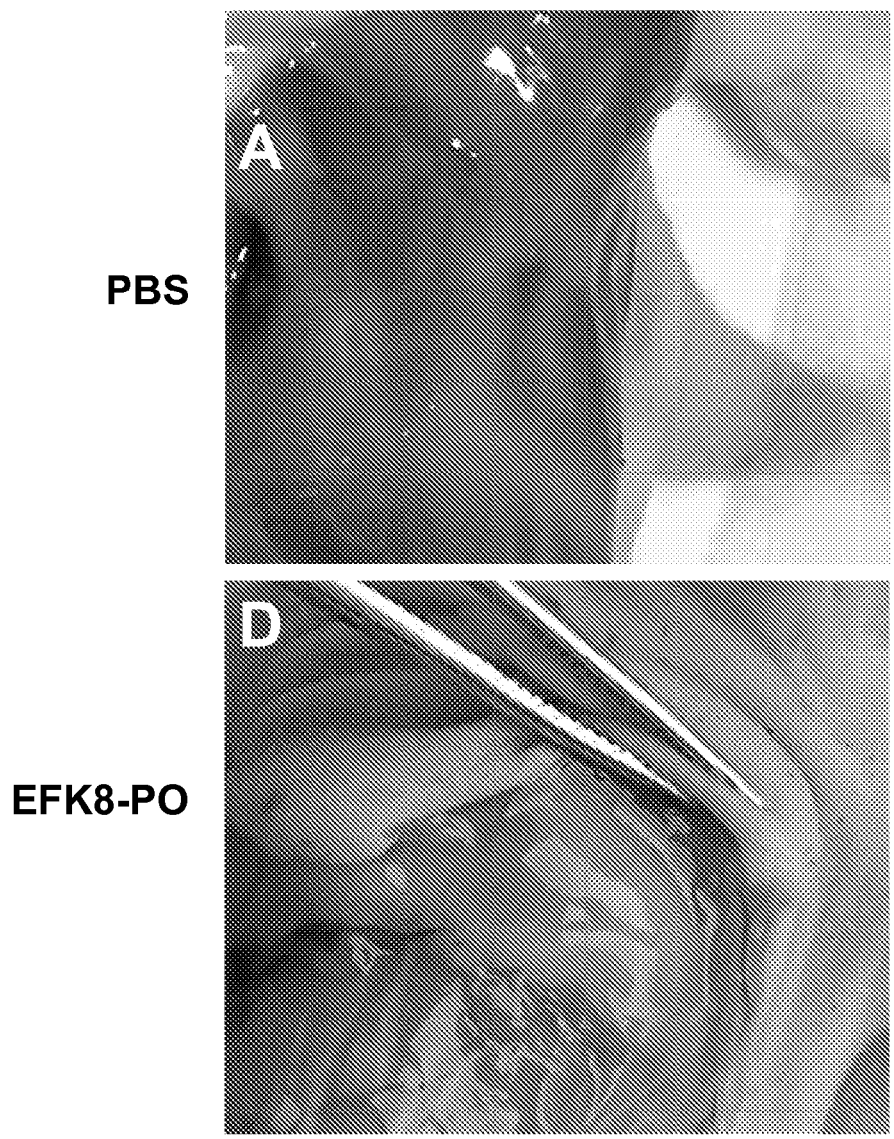

FIG. 8 is a blown-up version of FIGS. 7A and 7D.

DETAILED DESCRIPTION OF THE INVENTION

In tissue engineering, it is preferred if the scaffold provides a microenvironment that supports cell attachment, proliferation and differentiation, migration, tissue regeneration and appropriate 3D organization. It is known that natural polymers have superior bioactivity compared to synthetic polymers, whereas the mechanical properties of synthetic polymers are generally superior to those of naturally derived materials. However, scaffolds made of a single component or a single phase usually cannot provide such a preferred microenvironment that meets all or most of the above-stated characteristics. The combination of materials from different origins or with different properties could generate a hybrid material that meets the multiple needs of a scaffold for tissue engineering.

In its main embodiments, the present invention provides a hybrid (i.e., a combination of a synthetic and a natural material, such as a poloxamer and a self-assembling peptide) hydrogel scaffold suitable for at least human soft tissue engineering. In one embodiment, the scaffold of the invention consists of a polyoxyethylene-polyoxypropylene copolymer and a self-assembling peptide. In one embodiment, the copolymer and the self-assembling peptide lack or have minimal functional groups in order to minimize the chance of chemical reaction upon their combination into a scaffold or gel. In one embodiment, the hybrid hydrogel scaffold consisting essentially of a poloxamer and a self-assembling peptide have at least the same or greater mechanical strength and at least the same or greater bioactivity relative to a hydrogel scaffold made from either of the individual components alone.

Thus, it is an object of the invention that the hybrid hydrogel scaffolds of the invention to maintain the advantageous features of its individual components, for example, mechanical strength from the polyoxyethylene-polyoxypropylene copolymer component and favorable cellular functionality (viability, proliferation, migration, and differentiation) from its self-assembling peptide component. The lengths of the polymer blocks can be customized, and many different poloxamers exist that have slightly different properties. For the generic term "poloxamer," these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). For example, poloxamer 181 (P181) is equivalent to Pluronic L61.

As used herein, polymers are the substances of high molecular weight made up of repeating monomer units. The chemical reactivity of polymers depends upon the chemistry of their monomer units, but their properties depend to large extent on the way the monomers are put together. Polymer molecules may be linear or branched, and separate linear or branched chains may be joined by crosslinks. Polymers in which all the monomeric units are identical are referred to as homopolymers; those formed from more than one monomer type are called copolymers. Various arrangements of monomers, for example, A and B lead to formation of varieties of copolymers. As used herein, copolymers may be described as alternating copolymers, block copolymers, or graft copolymers. Pluronic is one of the most widely used block copolymer and forms heterogels.

Poloxamers or Pluronic (marketed by BASF Corporation) are the series of commercially available difunctional triblock copolymers of non-ionic nature. They comprise a central block of relatively hydrophobic polypropylene oxide surrounded on both sides by the blocks of relatively hydrophilic poly ethylene oxide. When the poloxamer has a PEO/PPO ration of 2:1, these molecules form micellar structures above critical micellar concentration when immersed in solution. They are regarded as PEO-PPO-PEO copolymers. Aqueous solutions of pluronic in presence of acids, alkalis, and metal ions are very stable. The poloxamers are readily soluble in aqueous, polar and non-polar organic solvents. The pluronic triblock copolymers are available in various grades differing in molecular weights and physical forms.

PEO/PPO ratio determines the phase behavior of pluronic like triblock copolymers. Modification of the structure and introduction of additional degree of freedom can be brought about by addition of solvents which are selective for block copolymers. The phase behavior that results depends upon relative volumes of polar PEO rich domains and of relatively nonpolar PPO rich domains.

Triblock copolymers generally have the characteristic property of thermoreversible gelation. The reversible thermal behavior of poloxamer 407 (pluronic F127) generally is observed in aqueous solutions of concentration range 20-30% w/w. They are liquid when refrigerated (4-5° C.) but turn into gel form when at room temperature. The gel thus formed is reversible on again cooling. When the pluronic is placed into cold water, at low concentrations; hydration layer surrounds the poloxamer molecule and hydrophobic portions are separated due to hydrogen bonding. With increasing temperature, desolvation of the hydrophilic chains occurs as the result of breakage of hydrogen bonds. This results into hydrophobic interactions amongst the polyoxypropylene domains and gel gets formed. Hydroxyl groups of the copolymer become more accessible due to hydration. The gel formed is micellar and the liquid micellar phase which is stable at low temperature undergoes conversion into cubic structure as the temperature increases, and the hexagonally packed cylinders are formed with increasing temperatures. The molecular weight and percentage of hydrophobic portion are determinant factors for gelling behavior. The gel formation occurs only when concentration is above critical micellar concentration. Reverse thermal gelation is the unique property of pluronic copolymers.

In one embodiment, the hybrid hydrogel scaffolds comprise a poloxamer that has a PPO component having an approximate molecular mass between about 3,000 g/mol and 5,000 g/mol. In one embodiment, the PPO component has an approximate molecular mass between about 3,500 g/mol and 4,500 g/mol. In one embodiment, the PPO component has an approximate molecular mass between about 3,750 g/mol and 4,250 g/mol. In one embodiment, the PPO component has an approximate molecular mass between about 3,900 g/mol and 4,100 g/mol. In one embodiment, the poloxamer has a polyoxyethylene content between about 60-80%. In another embodiment, the poloxamer has a polyoxyethylene content between about 65-75%. In one aspect, the poloxamer has a polyoxyethylene content of about 70%. In one embodiment, the poloxamer has a PPO component having an approximate molecular mass of about 4,000 g/mol and has a polyoxyethylene content of about 70% (i.e., poloxamer 407).

In one embodiment, the hybrid hydrogel scaffolds comprise a poloxamer consisting of a central hydrophobic block of polypropylene glycol flanked by two hydrophilic blocks of polyethylene glycol (PEG). In one embodiment, the approximate length of the propylene glycol block is between about 35-65 repeat units and the approximate length of the PEG blocks is between about 75-125 repeat units. In one embodiment, the approximate length of the propylene glycol block is between about 50-60 repeat units and the approximate length of the PEG blocks is between about 95-105 repeat units. In one embodiment, the approximate length of the propylene glycol block is about 56 repeat units and the approximate length of the PEG blocks is about 101 repeat units.

In other embodiments, the hybrid hydrogel scaffold can comprise one or more of the poloxamers listed in the Table below:

TABLE 3

Exemplary Commercial Poloxamers

| Pluronic | Poloxamer | a | b | Percent Content of Oxyethylene | Molecular Weight |
|---|---|---|---|---|---|
| L 44 NF | 124 | 12 | 20 | 44.8-48.6 | 2090-2360 |
| F 68 NF | 188 | 80 | 27 | 79.9-83.7 | 7680-9510 |
| F 87 NF | 237 | 64 | 37 | 70.5-74.3 | 6840-8830 |
| F 108 NF | 338 | 141 | 44 | 81.4-84.9 | 12700-17400 |
| F 127 NF | 407 | 101 | 56 | 71.5-74.9 | 9840-14600 |

"a" refers to the total number of ethylene oxide monomers and
"b" refers to the total number of propylene oxide monomers in the triblock copolymer; see Formula I above.

In one embodiment, the invention provides a scaffold for hard-tissue engineering, wherein the scaffold consists essentially of one or more types of poloxamer, and wherein the scaffold does not comprise a self-assembling peptide. As can be seen in Table 1, a hydrogel scaffold made of PO alone provides a high degree of cellular aggregation. Such aggregation indicates that such a scaffold may be amenable for tissue engineering applications relating to hard or compressed tissue, such as the lens of the eye, cartilage, and bone-type tissues.

In one embodiment, the self-assembling peptide is an oligopeptide that is 8-24 amino acids in length. In other embodiments, the self-assembling peptide is an oligopeptide that is at least 8, 9, 10, 11, 12, 13, 14, 15, 16, 17, 18, 19, 20, 21, 22, 23, or 24 peptides in length. In one embodiment, the self-assembling peptide is an oligopeptide that is 8-24 amino acids in length. In one embodiment, the self-assembling peptide has an amino acid sequence that alternates between hydrophobic side chains and charged side chains. In one embodiment, the self-assembling peptide is an eight-amino acid length oligopeptide. In one embodiment, the self-assembling peptide is an eight amino acid length oligopeptide that forms a left-hand double helix.

In one embodiment, the hybrid hydrogel scaffold of the invention is made from the co-gelation of the copolymer with the self-assembling oligopeptide. In one embodiment, this scaffold has improved mechanical strength and bioactivity relative to either of its individual components taken alone.

In one embodiment, the hybrid hydrogel "EFK8-PO" is made from the co-gelation of the synthetic polymer, poloxamer 407 ("PO"), and self-assembling oligopeptide, EFK-8. This scaffold comprising EFK8-PO has improved mechanical strength and bioactivity relative to either of its individual components taken alone.

EFK8 is one of the smallest peptides in the family of self-assembling peptides for use as biomaterials. EFK8 has an amino acid sequence that alternates between hydrophobic side chains and charged side chains, forming a special left-hand double helix that spontaneously undergoes association under physiological conditions.

In one embodiment, the hybrid hydrogel scaffold comprises a ratio of polyoxyethylene-polyoxypropylene copolymer to a self-assembling peptide that is about 100:1, 75:1, 50:1, 45:1, 40:1, 35:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 10:1, or about 5:1.

In one embodiments, the hybrid hydrogel scaffold comprises a polyoxyethylene-polyoxypropylene copolymer that is present in an amount of about 10-50%, 15%, 16%, 17%, 18%, 19%, 20%, 21%, 22%, 23%, 24%, 25%, 26%, 27%, 28%, 29%, or about 30% (w/v) (wherein "about" is used in these embodiments to mean less than 1%).

In one embodiments, the hybrid hydrogel scaffold comprises a self-assembling peptide that is present in an amount of about 0.25%, 0.50%, 0.75%, 1%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, or about 5% (w/v) (wherein "about" is sued in these embodiments to mean less than 0.1%).

In other embodiments, the hybrid hydrogel scaffold comprises a ratio poloxamer 407 to EFK-8 that is between about 5:1, 10:1, 15:1, 16:1, 17:1, 18:1, 19:1, 20:1, 21:1, 22:1, 23:1, 24:1, 25:1, 30:1, 35:1, 40:1, 50:1, 60:1, 70:1, 80:1, 90:1, or about 100:1.

In other embodiments, the hybrid hydrogel scaffold comprises PO present in an amount of about 10-50%, 10-40%, 10-30%, 15-25%, or about 20% (w/v) and EFK8 present in an amount of about 0.25-5%, 0.25-4%, 0.25-3%, 0.25-2%, 0.25-1.5%, 0.5-1.25%, 0.75-1.25%, or about 1% (w/v).

The hydrogel scaffold formed by co-gelation of poloxamer 407 and EFK8 has maintained the advantageous biological and physical features of its individual components, drawing its mechanical strength from poloxamer and its favorable cellular functionality (viability, proliferation, migration, and differentiation) from EFK8.

In one embodiment, the hybrid hydrogel scaffold is comprised of only about 1% EFK8, whereas to achieve a similar mechanical strength with a self-assembling peptide alone may require much higher concentrations and/or longer amino acid chain lengths. Given the high cost of manufacturing self-assembling peptides and the relatively weak mechano-elastic features of lower concentration and/or shorter amino acid chain length peptides, the addition of the significantly cheaper poloxamer 407 may mitigate this otherwise prohibitive issue.

In one embodiment, the hybrid hydrogel scaffold is comprised of only about 1% of a self-assembling peptide that is eight amino acids in length (% w/v). In another embodiment, the hybrid hydrogel scaffold is comprised of less than about 10%, 9%, 8%, 7%, 6%, 5%, 4%, 3%, 2%, or about 1% (w/v) of a self-assembling peptide that is eight amino acids in length.

In one embodiment, EFK8 has the amino acid sequence KFEFKFEF (SEQ ID NO:1). In another embodiment, EFK8 has the amino acid sequence FEFKFEFK (SEQ ID NO:2).

In other embodiments, the self-assembling peptide that is eight amino acids in length. includes, but is not limited to: KFEFKFEF (SEQ ID NO:1); FEFKFEFK (SEQ ID NO:2); RADARADA (SEQ ID NO:3); RARADADA (SEQ ID NO:4); AEAKAEAK (SEQ ID NO:5); RAEARAEA (SEQ ID NO:6); KADAKADA (SEQ ID NO:7); AEAEAHAH (SEQ ID NO:8); LELELKLK (SEQ ID NO:9); AEAEAKAK (SEQ ID NO:10); and HEHEHKHK (SEQ ID NO:11).

In other embodiments, the self-assembling peptide comprises at least eight amino acids comprising K and E at every other amino acid with F or other aromatics in between. For example, the self-assembling peptide can comprise the amino acid sequence FKFEFKFE (SEQ ID NO:12) or EFKFEFKF (SEQ ID NO:13).

In other embodiments, the hydrogels of the invention can comprise one or more bioactive molecules including but not limited to small molecules, proteins, peptides, and nucleic acids. Proteins can include for example growth factors, anti-differentiation factors, differentiation factors, cytokines, antibodies, hormones, etc. One example of an anti-differentiation factor is Y-27632, the selective Rho-associated kinase inhibitor 1. Nucleic acids can include siRNA, shRNA, antisense molecules, plasmids, etc. The hydrogels of the invention can also comprise viruses for gene expression or attenuated viruses in the context of vaccines. The hydrogels of the invention can also comprise nutrients, minerals, and other deliverables.

The hydrogels of the invention are tunable or can be adjusted with respect to its strength and elasticity by altering the ratio of the components of the bybrid hydrogel. The tunable nature allows for selection of the correct pore size for the tissue engineering applications. Skin requires pores of 50-400 nm, whereas bone requires much larger pores. By varying the ratio of the components, the pore size can be altered.

In most embodiments, the hydrogels of the invention are xeno-free, animal-free matrices, and therefore are generally nonimmunogenic. This is important for clinical applications. Addition of methylcellulose or hydroxymethylcellulose reduces immunogenicity relative to the use of recombinant extracellular matrix proteins contained in some hydrogels or matrigel for example. The shorter 8-mer self-assembling peptides have advantages over longer peptides such as a 16-mer in terms of immunogenicity, as the shorter peptide is much less immunogenic. Addition of methylcellulose to hybrid hydrogels comprising poloxamer and a self-assembling peptide further reduces immunogenicity Uses for the Hybrid Hydrogel Scaffolds.

In one embodiment, the scaffolds of the invention can be used as a matrix/scaffold for tissue engineering applications, including but not limited to bone growth or repair, as a skin substitute, etc. In one embodiment, the scaffolds can be used to reduce scar formation post-injury or trauma. In one embodiment, the scaffolds can be used to improve the appearance of preexisting scars. In one embodiment, the scaffolds can be used as a tissue filler agent for volume restoration of tissue defects. In one embodiment, the scaffolds can be used to reverse the signs of skin aging, including but not limited to reducing or reversing volume loss of skin tissue. In one embodiment, the scaffolds can be combined with growth factors or small molecules, nutrients, minerals, etc, to recapitulate the environment in vivo for the scaffold. In one embodiment, the scaffolds can be used as a delivery mechanism for drugs, etc. In one embodiment, the scaffolds can be used as a delivery mechanism for somatic and stem cells in transplantation settings.

In one embodiment, the invention provides coated tissue culture platforms (plates, wells, dishes, slides, etc.) wherein the coating comprises a thermoreversible hydrogel of the invention. This 2-D coated dish allows for cell passaging without the use of cell detachment agents such as trypsin, collagenase, or dispase, amongst others. This is achieved by placing the coated culture dish with cells and media into 4 degrees (or at a low temperature that is sufficient to cause the hydrogel to be in a liquid rather than a gelled state) briefly, until which point the cell-matrix interface changes from solid/gel phase to liquid phase, allowing cells to be recovered without enzymatic or chemical detachment. This method allows for preservation of cell surface markers and proteins.

The strength and elasticity of hydrogels can be altered by manipulating the ratio of the components of the bybrid hydrogel. The tunable nature of the hybrid hydrogels allows for selection of the correct pore size for the tissue engineering applications. For example, skin requires pores of 50-400 nm, whereas bone requires much larger pores. By varying the ratio of the components, pore size can be altered.

In one embodiment, the invention provides hybrid hydrogel compositions that are pro-aggregation when tissues are compact in nature, e.g. cartilage. This is facilitated by using a proaggregation ratio, higher in poloxamer, low to no self-assembling peptide, and modest amounts of methylcellulose, for example.

In one embodiment, the hybrid hydrogels of the invention can be used to make an artificial skin substitute using one of the hybrid combinations that has higher mechanical strength (this would be a hydrogel having a higher percentage of poloxamer and/or a higher percentage of methylcellulose and/or a higher percentage of extracellular matrix proteins as compared to other hybrid hydrogel applications).

In one embodiment, the scaffolds can be used as a hemostatic agent. The EFK8-PO hybrid hydrogel scaffold is effective as a hemostatic agent. When a bleeding hand was treated with EFK8-PO, bleeding stopped at one minute. When a bleeding hand was treated with PO alone, the hand was still bleeding at 10 minutes. Further, EFK8 alone is also effective as a hemostatic agent (data not shown).

In one embodiment, the scaffolds can be used in ophthalmic applications. For example, because the present hybrid hydrogels maintain the characteristics of its poloxamer component, they can be used as lens refilling material for injectable intraocular lens. In one embodiment, the poloxamer component for this application is Poloxamer 407 and is present in about 20-30% (w/v). In one embodiment, the poloxamer component for this application can be present in about 25% (w/v). In other embodiments, the hybrid hydrogel can further comprise carbopol and/or alginate and/or cysteine.

In one embodiment, the hybrid hydrogel scaffolds can be used to deliver liposomes. In one embodiment, the hybrid hydrogel comprises a Poloxamer 407 component present in the amount between about 20% and 30% (w/v).

In one embodiment, the hybrid hydrogel scaffolds can be used to deliver nucleic acids. In one embodiment, the hybrid hydrogel comprises a Poloxamer 407 component present in the amount between about 25% and 35% (w/v).

In one embodiment, the hybrid hydrogel scaffolds can be used as a mucoadhesive ophthalmic drug delivery system. In one embodiment, the hybrid hydrogel comprises poloxamer 407 present in at least 20% (w/v) such that the gel at physiological conditions is more dense or 'harder'.

In one embodiment, the hybrid hydrogel scaffolds can be used in intranasal applications, wherein the hybrid hydrogel comprises a poloxamer, a self-assembling peptide, and optionally one or more of a bioadhesive polymer such as methylcellulose, sodium carboxymethyl cellulose, hydroxypropyl methyl cellulose, carbopol 934P, chitosan glutamate and pluronic F127.

In one embodiment, the hybrid hydrogels can be used as controlled release drug delivery vehicles, where the pore size of the gel can be manipulated to control the diffusion of the drug from the gel. Alternatively, the hybrid hydrogel can be manipulated such that the kinetics of the phase transition from liquid to gel or from gel to liquid can be varied to alter the release of the drug.

In other embodiments, the hybrid hydrogels of the invention can be used as suppositories for both rectal and/or vaginal application.

In other embodiments, the hybrid hydrogels of the invention can be used as part of a periodontal gel formulation.

In other embodiments, the hybrid hydrogels of the invention can be used for transdermal and topical applications.

Generally, the hybrid hydrogels of the invention can be used in any application currently proposed or used for prior hydrogels.

Preparation of Hydrogels.

PO hydrogel was prepared by dissolving sterile poloxamer 407 (Sigma Aldrich, St. Louis, Mo.) in phosphate buffered saline (PBS) (pH 7.4) at 4° C. Phase transition between 4° C. and room temperature (23-25° C.) occurred at the concentration of 15.9% by weight, while the concentration for transition between room temperature and 37° C. was 14.3%. Once completely dissolved at low temperature, PO formed a clear solution which turned into a transparent gel when brought up to room temperature or 37° C. Self-assembling oligopeptide hydrogel was prepared by dissolving various concentrations of AcN-KFEFKFEF-$CONH_2$ (EFK8) (NeoMPS, San Diego, Calif.) in PBS with vortexing at room temperature. The hybrid hydrogel, EFK8-PO, was prepared by stirring 20% PO and 1% EFK8 in PBS at 4° C. until complete dissolution. In some cases, the solution contains sucrose in order to increase the homogeneity of salt crystallization.

Rheology.

The viscoelastic properties of 3 hydrogels were investigated with a, AR-G2 rheometer (TA Instruments, New Castle, Del.). The parameters of temperature sweep were set as follows: range 4-40° C., change rate 5° C./min, strain 2%; frequency 1 Hz. Three parameters were recorded: 1) storage modulus G' estimates the elastic component of mechanical strength, 2) lost modulus G'' estimates the viscous component of mechanical strength, and 3) phase difference Delta indicates the elastic or viscous property of a material. Zero degree of Delta implies a purely elastic material, while a purely viscous material has a Delta of 90 degrees. This same method can be used to analyze the viscoelastic properties of any of the scaffolds/hydrogels of the invention.

hAMSC Cell Culture and Encapsulation.

Abdominal subcutaneous adipose samples were obtained from 3 subjects undergoing cosmetic lipoaspiration. The study protocol was approved by the Stanford University institutional review board, and informed consent was obtained from all patients. Human adipose-derived MSCs (hAMSCs) were isolated using a modification of the method described by Dicker et al., "Functional studies of mesenchymal stem cells derived from adult human adipose tissue," *Exp Cell Res* 2005; 308:283-90, which is hereby incorporated by reference. Briefly, after gentle shaking with equal volume of Hank's Buffered Salt Solution (HBBS; Invitrogen, Carlsbad, Calif.), the mixture separated into two phases.

The lower phase (containing stem cells, adipocytes and blood) was resuspended in HBSS containing 0.075% collagenase type I (Sigma Aldrich), and enzymatically dissociated for 1 hr at 37° C. with gentle shaking. The collagenase was inactivated by adding an equal volume of DMEM (Invitrogen) supplemented with 10% fetal bovine serum (FBS) and incubated 10 min at room temperature. The mixture was then centrifuged at 1,500 rpm for 5 min at 20° C. The cellular pellet was resuspended in red blood cell lysis buffer (eBioscience, San Diego, Calif.) to eliminate erythrocytes and sequentially passed through 100, 70, and 40 μm mesh filters to remove cell debris. The cell filtrate was then diluted with an equal amount of HISTOPAQUE-1077 (Sigma Aldrich) and centrifuged at 5000×g for 30 min to separate the hAMSC fraction. Cells were resuspended in DMEM containing 10% FBS and plated at a concentration of $1-5\times10^6$ cells/75 $cm^2$. Cells were serially passaged upon reaching 70%-80% confluence by detaching with 0.25% trypsin-EDTA (Invitrogen).

hAMSCs were confirmed to meet the minimal criteria for defining multipotent MSCs according to previously described methods [Dominici et al., "Minimal criteria for defining multipotent mesenchymal stromal cells. The International Society for Cellular Therapy position statement," Cytotherapy 2006; 8:315-7.]. First, hAMSCs were plastic-adherent when maintained in standard culture conditions using tissue culture flasks. Second, RT-PCR studies confirmed hAMSCs highly expressed CD73, CD90, and CD105, but did not express CD14, CD19, CD34, CD45, or HLA class II (data not shown). Third, hAMSCs were able to differentiate to osteoblasts, adipocytes and chondroblasts under standard in vitro differentiating conditions.

Cells were encapsulated in the appropriate hydrogel by gently mixing hAMSCs with PO, EFK8, or EFK8-PO at a final concentration of $1\times10^6$ cells/ml. When seeding hAMSCs in PO or EFK8-PO, hydrogels were kept on ice to prevent premature gelation. Fifty μL of the aliquot of hydrogel/cell mixture was quickly transferred into a 96-well microplate. Encapsulated hAMSCs were then incubated at 37° C. for 5 min to induce gel formation. One hundred μL of DMEM medium was then added into each well. Fresh medium was changed 3 times within the first 30 min in order to neutralize the acidic pH of the hydrogels, and then changed every other day during culture. After various treatments described below and at the appropriate time points, a 1000 μL pipette tip was cut at its distal end to facilitate our ability to gently draw up 50 μL of encapsulated hAMSCs from the top of the well. Cells were then gently placed onto a slide to allow for examination under light field microscopy. This process was repeated 3 times per well, allowing for assessment of a total of 3 different depth layers (top, middle, and bottom) of the encapsulated cell mixture. This method of encapsulation can generally be used for encapsulating most cell-types in the scaffolds described herein.

Cell Viability.

hAMSCs were encapsulated in PO, EFK8, or EFK8-PO and cultured in a 37° C. humidified 5% $CO_2$ incubator for 3 hrs, 1, 3, 6, 10, or 14 days. Fifty μL of cells was then mixed with an equal volume of 1% trypan blue and observed under light microscopy. Trypsin-EDTA (0.25%) was used to separate cells when cell aggregation occurred. Viability was calculated as the percentage of living cells over total cells.

Cell Proliferation.

hAMSC proliferation was determined using both the WST-1 Cell Proliferation assay (Roche, Palo Alto, Calif.) as previously described in Abu Ubeid A, Zhao L, Wang Y, Hantash B M. Short-Sequence Oligopeptides with Inhibitory Activity against Mushroom and Human Tyrosinase. J Invest Dermatol 2009; 129:2242-9, which is hereby incorporated by reference, and using a BrdU incorporation assay (Roche) according to the manufacturer's protocol, respectively. $1\times10^4$ hAMSCs were encapsulated as described above, and then added to each well of a 96-well flat-bottomed microplate. After gelation, 100 μL of DMEM medium was added to the top of each well, then the plate was placed in a 37° C. humidified 5% $CO_2$ incubator. Medium was replaced every other day. WST-1 was added at 4 hours prior to reaching day 1, 2, 3, or 4 post-incubation, then placed at 37° C. for an additional 4 hrs in the dark, and the absorbance at 480 nm was read using the HTS 7000 Plus Bio Assay reader (Perkin Elmer, Waltham, Mass.). BrdU was added 0, 1, 2, 3, and 4 days following the initial incubation, then plates were placed at 37° C. for an additional 24 hrs, and the absorbance at 370 nm was read. Three replicates were measured for each permutation. Wells containing medium and hydrogel but no cells served as background controls. For BrdU, a no hydrogel control was also evaluated.

In Vitro Induction of Adipogenic and Osteogenic Cell Differentiation.

hAMSCs were encapsulated in PO, EFK8, and EFK8-PO as above. Adipogenic or osteogenic differentiation was induced by culturing cells in adipogenic or osteogenic differentiation medium (AD-medium or OS-medium, respectively, Cell Applications, San Diego, Calif.) for 7 days or 14 days, respectively, according to our previously published method, which is hereby incorporated by reference, Zhao L et al., "TGF-beta 1 Induces Osteogenic Differentiation of Murine Bone Marrow Stromal Cells," *Tissue Eng Part A* 2009, In press. Fresh induction media was added to every other day.

Red oil staining was used to confirm hAMSC adipogenic differentiation. Cells were washed with PBS and fixed with 10% formalin for 20 min. Cells were then washed twice with PBS, once with 60% isopropyl alcohol, stained with Oil Red O solution (Sigma-Aldrich) for 15 min, washed with PBS once more, and then observed by light field microscopy, Hata K et al., "A CCAAT/enhancer binding protein beta isoform, liver-enriched inhibitory protein, regulates commitment of osteoblasts and adipocytes," *Mol Cell Biol,* 2005, 25(5):1971-1979, which is hereby incorporated by reference.

Alkaline Phosphatase (ALP) staining was used to detect mineralization in hAMSCs during osteogenic differentiation. After culturing encapsulated hAMSCs for 14 days in the various hydrogels, the medium was aspirated and cells were stained with StemTag ALP (Cell Biolabs, San Diego, Calif.) according to the manufacturer's protocol. Briefly, after washing twice with PBS, cells were exposed to fixing solution for 2 min, then washed again with PBS and incubated with StemTAG ALP staining solution for 30 min in the dark. ALP staining solution was aspirated and cells were then washed with PBS and observed under light microscopy. Alizarin red S staining was used to detect extracellular calcium deposition in hAMSCs during osteogenic differentiation according to our previously published method, which is hereby incorporated by reference, Zhao L et al., "TGF-beta 1 Induces Osteogenic Differentiation of Murine Bone Marrow Stromal Cells," *Tissue Eng Part A* 2009, In press Assessment of In Vivo Adipogenic Differentiation Potential.

All mouse experiments were conducted in accordance with the Guide for the Care and Use of Laboratory Animals and were approved by each Institution's respective Administrative Panel on Laboratory Animal Care. hAMSCs were encapsulated in PO, EFK8, and EFK8-PO hydrogels at a final concentration of $1 \times 10^6$ cells/ml and mixed gently in the hydrogels. PO and EFK8-PO were kept on ice to prevent premature gelation during the seeding process. Two hundred µL of each encapsulation was injected subcutaneously using 1 ml syringes into the dorsal neck area of female nude mice (8 weeks of age). Two hundred µL of PBS was used as a control. The nude mice were then allowed to recover, and then returned to their cages. After 30 days, mice were sacrificed using $CO_2$ euthanasia and dorsal neck skin harvested immediately. Each sample was embedded in OCT compound (Miles, Elkart, Ind.) and processed for immunohistochemistry studies according to a modified version of the protocol described in Hemmrich, K et al., "Implantation of preadipocyte-loaded hyaluronic acid-based scaffolds into nude mice to evaluate potential for soft tissue engineering," *Biomaterials,* 2005, 26(34):7025-37, which is hereby incorporated by reference.

Immunohistochemistry Studies.

Specimens were frozen sectioned using either vertical or horizontal slices 5-10 µm thick, then post-fixed in 100% cold acetone at −20° C., blocked for 1 hr with goat serum and then incubated with the appropriate mouse anti-human nuclei monoclonal primary antibody (Chemicon, Billerica, Mass.) at the desired dilution (1:50 to 1:250) overnight at 4° C. Signal was detected using the Vectastain ABC Elite Mouse/Rabbit/Goat IgG detection kit (Vector Laboratories, Burlingame, Calif.) following the manufacturer's protocol. Diaminobezidine (Sigma Aldrich) was used as the enzyme substrate as it forms an easily detectable brown precipitate. Counterstaining was performed using Harris hematoxylin (Sigma Aldrich) for 10 min with a regression step in acid alcohol.

Statistical Analysis.

All experimental data herein represent a minimum of 3 independent experiments. The results were averaged and standard error of the mean was calculated for all conditions using Microsoft Excel. P values are shown in the figure legends and were taken to be statistically significant at $p<0.05$.

All references cited herein are hereby incorporated by reference in their entirety.

EXAMPLES OF THE INVENTION

Example 1

Hybrid Hydrogel Scaffold

Herein, the characteristics of a novel hybrid hydrogel scaffold (EFK-PO) composed of poloxamer 407 (PO) and the self-assembling oligopeptide EFK8, was examined in vitro and in vivo. Rheological tests showed that the storage modulus of EFK8-PO increased by 4 orders of magnitude compared to that of EFK8 alone, indicating that EFK8-PO integrates PO's high and tunable mechanical strength and integrity with the superior bioactivity of EFK8. When human adipose-derived mesenchymal stem cells (hAMSCs) were cultured in PO, we observed severe aggregation. Conversely, almost no aggregation was observed in EFK8 or EFK8-PO after 6 days of culture. hAMSC viability in all 3 hydrogels remained above 80% after 2 weeks of culture. EFK8 and EFK8-PO significantly increased hAMSC proliferation rates. In addition, EFK8- and EFK8-PO- but not PO-encapsulated hAMSCs differentiated into adipocytes or osteoblasts when exposed to appropriate induction medium, suggesting EFK8 supports hAMSC multipotency in vitro. Moreover, only EFK8-PO supported hAMSC engraftment and adipogenic differentiation post-transplantation into nude mice. Immunohistochemical analysis confirmed the new tissue was human in origin.

Thus, the novel hydrogel formed by co-gelation of poloxamer 407 and EFK8 substantially improved viscoelasticity as evidenced by a dramatic increase in the storage modulus and shift of the phase difference Delta towards elasticity. Moreover, the hybrid biomaterial maintained EFK8's advantageous bioactivity profile (viability, proliferation, migration, and differentiation) in both in vitro and in vivo tests of hAMSCs. Achieving a similar mechanical strength profile with a self-assembling peptide requires much higher concentrations and/or longer amino acid chain lengths. Given the high cost of manufacturing self-assembling peptides and the relatively weak mechanoelastic features of lower concentration and/or shorter amino acid chain length peptides, the addition of the significantly cheaper poloxamer 407 may mitigate this otherwise prohibitive issue. Because the present studies were conducted with hAMSCs, the poloxamer-oligopeptide hybrid hydrogels of the invention can be used as a 3D scaffold for stem cell-based soft tissue engineering in general.

Viscoelastic Property of the Hydrogels.

Figure 1A:
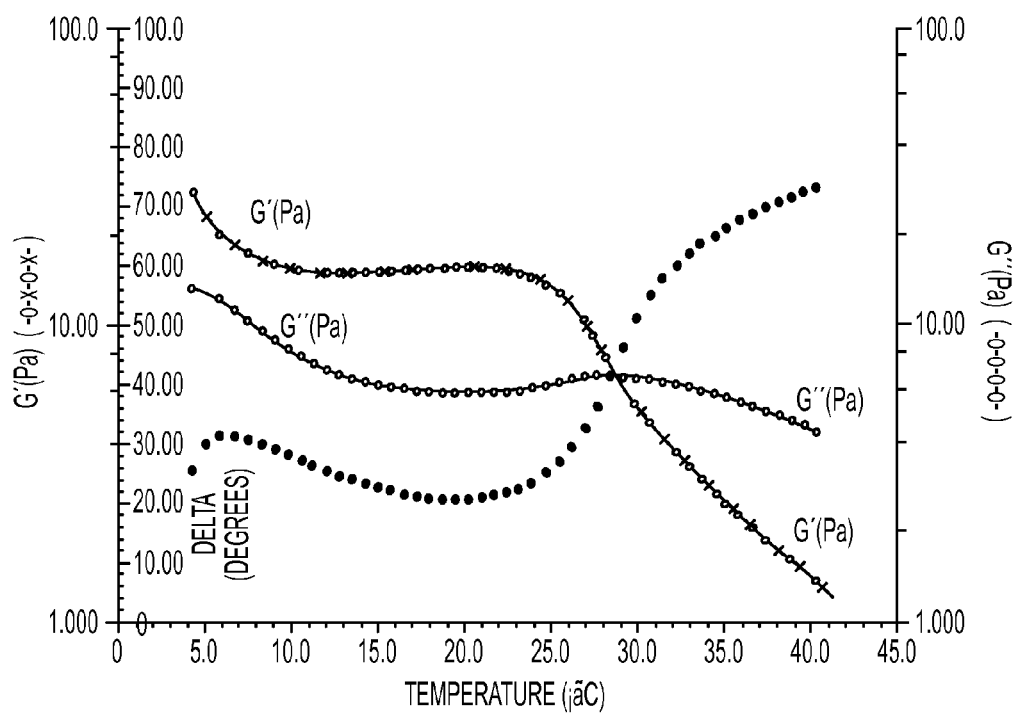
FIG. 1. Viscoelastic properties of 3 hydrogels. (A) EFK8, (B) PO, (C) EFK8-PO.
Figure 1B:
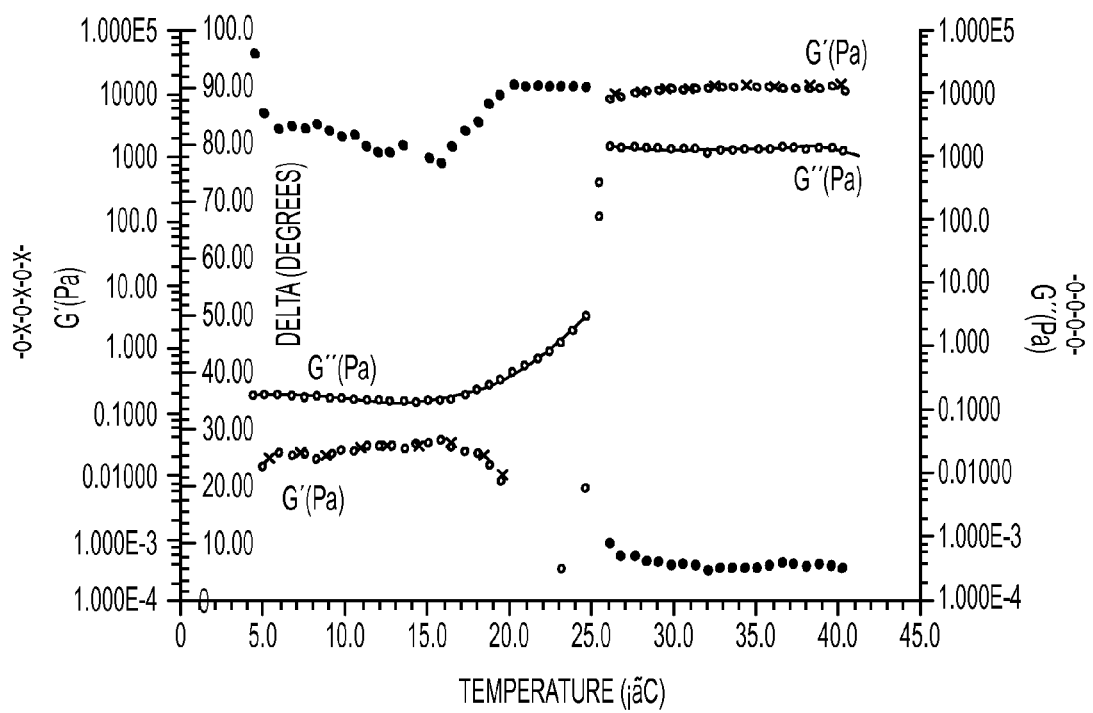
Figure 1C:
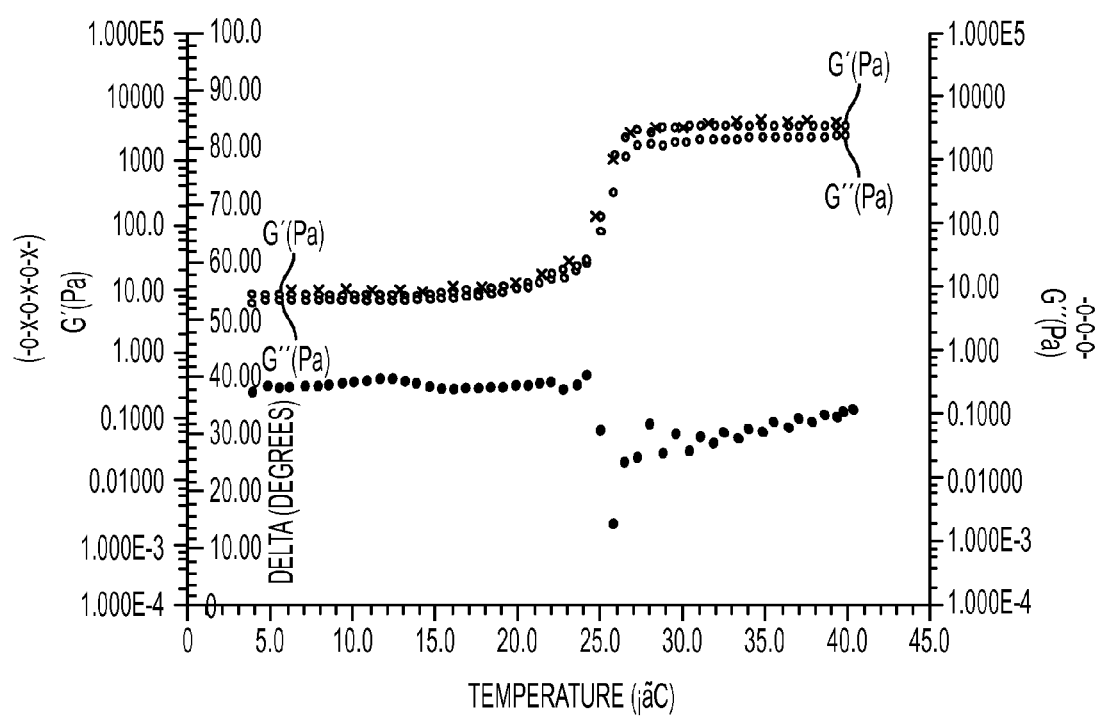

To determine the mechanical properties of PO, EFK8, and EFK8-PO hydrogels, we performed rheological analyses. The viscoelastic behaviors of EFK8 (1% w/v in PBS), PO (20% w/v in PBS), and EFK8-PO (20% w/v PO plus 1% w/v EFK8, both in PBS) hydrogels are illustrated in FIG. 1. At 25° C., G' of EFK8 hydrogel was ~10.5 Pa and G" was ~6.2 Pa. At 37° C., G' decreased to 2 Pa, and G" slightly decreased to 5 Pa. Phase difference Delta increased from 30 degrees to 70 degrees (FIG. 1A). These results suggested that EFK8 hydrogel turned more viscous with increasing temperatures. EFK8 hydrogel was very weak and less viscous both at room temperature and 37° C. FIG. 1B shows that PO hydrogel experienced an abrupt phase transition at ~25° C., where G' increased by 6 orders of magnitude and G" increased by 4 orders of magnitude, respectively. FIG. 1C illustrates the viscoelastic behavior of EFK8-PO. This hybrid hydrogel also showed a phase transition at 25° C. Before transition, both G' and G" of the mixture were close to those of EFK8, whereas after phase transition the elastic and viscous moduli approached those of PO, indicating that EFK8 and poloxamer macromolecules dominated the viscoelastic properties before and after the phase transition, respectively. However, as shown in FIG. 2C, the phase difference Delta did not change in EFK8-PO upon phase transition. These data suggest that EFK8-PO integrated PO's mechanical strength and integrity, allowing it to become stronger than EFK8 alone.

Morphology and Distribution of Hydrogel-Encapsulated hAMSCs.

Poloxamer 407 has been reported to provide a suitable 3D environment for differentiation of BMSCs into adipocytes [Vashi A V et al., "Adipose differentiation of bone marrow-derived mesenchymal stem cells using Pluronic F-127 hydrogel in vitro," *Biomaterials* 2008; 29:573-9, which is hereby incorporated by reference). However, the biological characteristics of EFK8 and EFK8-PO hydrogels have not yet been studied. We therefore cultured hAMSCs in PO, EFK8, and EFK8-PO hydrogels. hAMSCs generated in our lab met the minimal criteria for defining multipotent MSCs (Dominici M et al. (2006)). FIG. 2 illustrates the morphology and distribution of hAMSC encapsulated in PO, EFK8, and EFK8-PO for up to 14 days in culture. As shown in FIG. 2A, PO induced >90% of hAMSCs to aggregate after just 3 days in culture. In fact, we observed cell aggregation as early as 20 hrs post-incubation (data not shown), and this continued at 6 days (FIG. 2B) and 10 days (FIG. 2C) post-incubation.

EFK8 hydrogel induced minimal cell aggregation (<3-5%), with rare cell clusters observed after 3 days (FIG. 2D) or 6 days (FIG. 2E) of culture. At 10 days, we observed ~10% of cells aggregated (FIG. 2F). In sharp contrast to both PO and EFK8 hydrogels, EFK8-PO appeared to promote dispersion of hAMSCs homogeneously across the hydrogel after 3 days in culture (FIG. 2G). Slight cell aggregation was observed at day 6, but most cells remained homogeneously dispersed (FIG. 2H). A single cluster of aggregated cells was detected after 10 days of culture in EFK8-PO hydrogel (FIG. 2I).

Viability and Proliferation of Hydrogel-Encapsulated hAMSCs.

Next, we investigated cellular viability in PO, EFK8, and EFK8-PO hydrogels. FIG. 3 shows that cellular viability in all 3 hydrogels remained above 80% after 14 days of culture, indicating that PO, EFK8, and EFK8-PO were not significantly cytotoxic to hAMSCs. FIG. 3 also illustrates that there was no statistically significant difference ($p > 0.05$) in hAMSC viability for the 3 individual hydrogels when comparing identical time points.

The proliferation of hAMSCs in the 3 hydrogels was tested using the WST-1 proliferation assay. After cell encapsulation and culturing in EFK8 and EFK8-PO hydrogels, hAMSCs began a period of rapid proliferation (FIGS. 4B & 4C). This was confirmed by the significant difference in the optical density value between days 1 and 2 ($p < 0.05$). This continued for at least 4 days of culture, indicating that both EFK8 and EFK8-PO promote cell proliferation. However, cell proliferation was not observed in PO hydrogel alone (FIG. 4A). Since cells aggregated dramatically in PO hydrogel after 1 day of culture, we also assessed proliferation rates using the BrdU incorporation method. FIG. 4D illustrates that EFK8-PO enjoyed a similar proliferation rate as that observed for hAMSCs cultured on EFK8 alone, while rates for PO mirrored those observed when using WST-1 (FIG. 4A).

Multipotency of Hydrogel-Encapsulated hAMSCs In Vitro.

We examined the cell surface marker expression pattern of hAMSCs encapsulated in EFK8 and EFK8-PO but not in PO since the latter caused severe aggregation. After 2 weeks of culture, RT-PCR studies showed hAMSCs expressed CD73, CD90, and CD105 but were negative for CD14, CD19, CD34, CD45, and HLA class II (data not shown).

We next tested if hAMSCs maintained their multipotency when encapsulated in EFK8 and EFK8-PO. After 4 days of adipogenic induction, small vacuoles were observed within 42±6% and 38±3% of hAMSCs cultured in EFK8 and EFK8-PO, respectively (Table 1). After 7 days of induction, the vacuoles increased to occupy most of the cytoplasm, whereas no vacuoles were observed in the absence of differentiation medium (Table 1). Oil Red O staining was positive in 68±8% and 56±8% for EFK8 and EFK8-PO encapsulated hAMSCs (FIGS. 5C & 5D), respectively. Minimal staining was observed when hAMSCs were treated with control culture medium (FIGS. 5A & 5B). After 14 days of incubation with osteogenic differentiation medium, hAMSCs encapsulated in EFK8 and EFK8-PO were found to stain positively for ALP 88±9% and 72±6% (FIGS. 6C & 6D), respectively. Extracellular calcium deposition, as detected by alizarin red S staining, was observed in 54±7% and 46±5% of hAMSCs encapsulated in EFK8 and EFK8-PO, respectively (Table 1). Minimal ALP or alizarin red S staining was observed in the absence of osteogenic differentiation medium (FIGS. 6A & 6B and Table 1).

Adipogenic Differentiation of Hydrogel-Encapsulated hAMSCs In Vivo.

hAMSCs were encapsulated in the hydrogels and then each mixture or PBS alone was injected subcutaneously into the dorsal necks of nude mice necks. At 30 days post-injection, we observed the presence of a white to yellow tissue just above the muscle fascial plane for EFK8-PO encapsulated hAMSCs (FIG. 7D) but not in the mice injected with PBS alone (FIG. 7A). We did not observe new adipose tissue in mice treated with either EFK8 or PO alone (data not shown) Immunohistochemical analysis of the adipose tissue with an antibody specific to human nuclei showed positive diaminobenzidine staining (brown color) in the EFK8-PO (FIGS. 7E & 7F) but not in the PBS cohort (FIGS. 7B & 7C). To ensure only the location-appropriate differentiation occurred, we stained with alizarin red S and ALP. We found no evidence of mineralization or extracellular calcium deposition in any of the conditions tested.

Summary.

In tissue engineering, the scaffold must provide a microenvironment that supports cell attachment, proliferation and differentiation, migration, tissue regeneration and appropriate 3-D organization [26]. However, scaffolds made of a single component or a single phase usually cannot provide such an ideal microenvironment that meets all or most of the above requirements. The combination of materials from different origins or with different properties could generate a hybrid material that meets the multiple needs of a scaffold for tissue engineering.

The objective of this study was to develop a hydrogel scaffold suitable for human soft tissue engineering. It is well known that natural polymers have superior bioactivity compared to synthetic polymers, whereas the mechanical properties of synthetic polymers are general superior to those of naturally derived materials. Herein, it was postulated that a combination comprised of a synthetic polymer and natural material may result in a hybrid material that incorporates the advantages of each of its individual components. In this study, the co-gelation of the synthetic polymer, poloxamer 407, and self-assembling oligopeptide, EFK-8, produced a hybrid hydrogel (EFK8-PO) with improved mechanical strength and bioactivity relative to either of the individual components taken alone.

In this study, the storage modulus G' of EFK8-PO increased by 4 orders of magnitude relative to that of PE at 37° C., while the lost modulus G" also increased by 3 orders of magnitude, demonstrating that poloxamer 407 successfully reinforced the hydrogel system. The viscoelastic properties revealed that there was little, if any, chemical reaction in the hybrid hydrogel (FIG. 1). The hybrid hydrogel was prepared by simply dissolving the 2 components in PBS. This was planned, as EFK8 and poloxamer 407 were specifically chosen due to their lack of functional groups, minimizing the chance of chemical reaction upon combination. Based on this, and without being bound by theory, it was postulated that EFK8 assumed its native β-sheet and nanofiber networking structure at low temperature prior to phase transition. The network illustrated inadequate strength to prevent the movement of poloxamer molecules. Increasing the temperature still facilitated poloxamer molecular movement allowing the physical cross-linking of polyoxypropylene groups and consequent gelation of poloxamer molecules.

It is noted that the loose interactions of the 2 components are desirable for tissue engineering since it is expected not to jeopardize the bioactivity of EFK8, or the ability of cells and nutrients to move inside the hydrogel scaffold. Moreover, poloxamer 407 successfully reinforced the hydrogel as evidenced by its abrupt phase transition at ~25° C., where G' increased by 6 orders of magnitude and G" increased by 4 orders of magnitude. This is consistent with poloxamer's temperature-dependent increase in viscoelasticity (FIG. 1). The trend of Delta also showed that phase transition changed the material from an almost purely viscous state at low temperature (Delta close to 90 degrees) into a nearly pure elastic state (Delta close to 0 degrees) of hydrogel at elevated temperature. These data suggest that EFK8-PO integrated PO's mechanical strength and integrity, allowing it to become stronger than EFK8 alone.

The bioactivity of EFK8-PO hydrogel was also improved as demonstrated by the homogeneous dispersion of hAMSCs in EFK8-PO gel compared to PO alone (FIG. 2). hAMSC viability and proliferation tests indicated that the combination did not induce cytotoxicity. This favorable result was complemented by the fact that hAMSCs were also found to maintain their multipotency in vitro (FIGS. 5 & 6). Although it was attempted to determine hAMSC multipotency in PO hydrogel, similar to a previous study, Vashi A V et al., "Adipose differentiation of bone marrow-derived mesenchymal stem cells using Pluronic F-127 hydrogel in vitro," *Biomaterials*, 2008, 29(5):573-579, herein severe cell aggregation was observed and this line of experimentation was abandoned (FIG. 2, panels A-C). The reason for the severe aggregation with poloxamer 407 may be due to the balance of hydrophobicity and hydrophilicity for this macromolecule. Poloxamer 407 is a completely synthetic and nonionic polymer; therefore, it lacks the necessary charge groups that can serve as cell anchoring points. Thus, poloxamer 407 alone may not be an appropriate scaffolding material for applications that require cell-matrix interactions, even though the data herein suggests that poloxamer 407 promotes cell-cell interactions and cell migration.

Cell aggregation was also observed in the EFK8-PO hydrogel after 10 days of culture (FIG. 2I). The minimal aggregation behavior of hAMSCs in the hybrid hydrogel indicated that the high bioactivity of EFK8 dominated at the initial stage of cell culture. This was evidenced by the fact that EFK8-PO encapsulated hAMSCs appeared homogenously dispersed similar to what we observed with PE alone (FIG. 2, panels G & H). This is consistent with the notion that charge groups on EFK8 can successfully anchor hAMSCs, as would be expected for a cell-matrix interaction. It is unclear how strong this interaction is; therefore, one cannot speculate on whether migration was hindered or facilitated by this feature. Cell aggregation behavior could be one of the most important reasons for the difference of cell proliferation behavior in the 3 hydrogels. Notwithstanding, the data indicates that combining EFK8 with PO improves cell bioactivity relative to PO alone, closely matching that observed with EFK8 alone.

Without being bound by theory, it is postulated that when EFK8 and poloxamer 407 are combined, each assumes the molecular structure that it would when in isolation. Thus, poloxamer physically cross-links hydrophobic polyoxypropylene blocks at the micelle center with hydrophilic polyoxyethylene blocks surrounded by water. Since EFK8 self-assembles into a nanofibrillar network, it mimics native extracellular matrix more closely than poloxamer. The formation of such a nanofibrillar network in the hybrid hydrogel could be the reason for its high bioactivity.

To confirm the significance of the in vitro findings, the adipogenic differentiation potential of hydrogel-encapsulated hAMSCs was also investigated with respect to in vivo differentiation. At 1 month post-transplantation into nude mice, it was observed that only EFK8-PO supported hAMSC engraftment and adipogenic differentiation (FIG. 7). Importantly, the new fat tissue was confirmed to be of human origin (FIGS. 7E and 7F), although it cannot rule out that hAMSCs did not also induce mouse fat differentiation via release of pro-adipogenic growth factors or cytokines. Of additional significance, we found no evidence of bone mineralization or extracellular calcium deposition in the tissue examined, confirming that location-specific cues continued to signal appropriately. The lack of heterotopic tissue formation provides an additional level of safety and specificity control for the hybrid hydrogel. In terms of PO, its pro-aggregation properties likely contributed to its inability to induce adipogenesis. This property of PO may be more suitable for engineering compactly organized tissues such as cartilage. With regard to EFK8, it is hypothesized that its low viscoelasticity resulted in rapid dispersion upon injection. This is supported by the lack of a bleb at the injection site shortly after transplantation, suggesting the possibility that EFK8 did not promote the 3-D structure and microenvironment necessary for engraftment and adipogenesis.

To date, self-assembling peptide-based hydrogels have suffered from reduced mechanical strength relative to non-peptide based counterparts. This has been manifest by characteristics such as low G' and G", and a Delta close to 90 degrees reflecting an almost purely viscous state at low temperature. For many tissue engineering applications, this key limitation has outweighed the benefit of improved bioactivity over traditional synthetic hydrogels, leading to a significant translational barrier for self-assembling peptides as biomaterials. To overcome these limitations, the present invention provides hybrid hydrogels, including a hybrid hydrogel made by co-gelation of poloxamer 407 and EFK8. The invention successfully demonstrated that the addition of poloxamer 407 to EFK8 resulted in substantially improved viscoelasticity as evidenced by a dramatic increase in the storage modulus and shift of the phase difference Delta towards elasticity. Moreover, the hybrid biomaterial maintained EFK8's advantageous bioactivity profile (viability, proliferation, migration, and differentiation) in both in vitro and in vivo tests of hAMSCs. Achieving a similar mechanical strength profile with a self-assembling peptide requires much higher concentrations and/or longer amino acid chain lengths. Given the high cost of manufacturing self-assembling peptides and the relatively weak mechanoelastic features of lower concentration and/or shorter amino acid chain length peptides, the addition of the significantly cheaper poloxamer 407 may mitigate this otherwise prohibitive issue. As the studies herein were conducted on hAMSCs, the poloxamer-octapeptide hybrid hydrogel provides a 3-D scaffold for stem cell-based soft tissue engineering.

Example 2

Hydrogels for 2-D Cell Culture Applications

To examine preferred compositions for 2-D cell culture, hydrogels containing various concentrations of poloxamer and methylcellulose were evaluated for integrity in presence of cell culture medium. F127 and methylcellulose were added to PBS, and mixed until ingredients went into solution. Each hydrogel was overlayed into wells and the 24 well plate was put in a 37° C. incubator to solidify hydrogels and then warm (37° C.) medium was added into each well. Table below summarizes data from those studies and provides for preferred compositions.

TABLE 4

Hydrogels Comprising Poloxamer and Methylcellulose

| F127:Methyl-cellulose (w/v in PBS) | Ability to change phase from solid to liquid and back | Gel integrity with medium | Transluscence of hydrogel in 24 well plates |
| --- | --- | --- | --- |
| 22:0  | +++++ | –     | +++++ |
| 22:1  | +++++ | –     | +++++ |
| 22:5  | –     | N/A   | +     |
| 22:10 | –     | N/A   | –     |
| 11:1  | –     | N/A   | +++++ |
| 11:2  | –     | N/A   | +++++ |
| 11:4  | ++++  | N/A   | +++++ |
| 12:3  | +++   | ++++  | +++++ |
| 18:2  | ++++  | –     | ++++  |
| 14:1  | +     | –     | ++++  |
| 13:2  | +++   | +     | +++++ |
| 15:3  | ++++  | +++++ | ++++  |
| 18:3  | ++++  | +++++ | +++   |
| 18:4  | +++   | +++++ | +++   |
| 15:4  | +++   | +++++ | ++++  |

Thus, in some embodiments, the invention provides a hydrogel comprising a cellulose between about 1-5% (w/v) and a poloxamer between about 10-25% (w/v). In one embodiment, the cellulose is methylcellulose. In one embodiment, the poloxamer comprises a PEO-PPO-PEO block copolymer. In one embodiment, the poloxamer comprises a PEO-PPO-PEO block copolymer with an approximate average molecular weight between about 11,500 and 14,000. In one embodiment, the hydrogel comprises methylcellulose present at about 1-4% (w/v) and poloxamer 407 present at about 10-20% (w/v).

What is claimed:

1. A hybrid hydrogel scaffold, the scaffold comprising:
(a) about 0.75% to about 1.25% EFK8 (w/v);
(b) about 20% poloxamer 407 (w/v);
wherein the scaffold provides a microenvironment that: (i) substantially prevents the aggregation of cells, (ii) promotes cell proliferation at a rate that is improved or substantially similar to a hydrogel scaffold made from EFK8 alone, and (iii) has viscoelastic properties that are improved or substantially similar to a hydrogel scaffold made from poloxamer 407 alone; and
(c) mesenchymal stem cells;
wherein the mesenchymal stem cells are capable of differentiation when the scaffold is transplanted in vivo.

2. The scaffold of claim 1, further comprising one or more of the following:
methylcellulose, carboxymethylcellulose, hydroxypropylmethylcellulose, bioactive molecules, somatic cells, stem cells, nutrients, minerals, and any combination thereof.

3. The scaffold of claim 1, wherein EFK8 is present in an amount of about 1% (w/v), and poloxamer 407 is present in amount of about 20% (w/v).

4. The scaffold of claim 1, wherein the scaffold was gelled from a solution comprising EFK8 present in an amount of about 1% (w/v) in the solution and poloxamer 407 present in an amount of about 20% (w/v) in the solution.

* * * * *